United States Patent
Stroebech

(10) Patent No.: US 12,376,984 B2
(45) Date of Patent: Aug. 5, 2025

(54) STOMAL SENSOR PATCH

(71) Applicant: Coloplast A/S, Humlebaek (DK)

(72) Inventor: Esben Stroebech, Hoersholm (DK)

(73) Assignee: Coloplast A/S, Humlebaek (DK)

( * ) Notice: Subject to any disclaimer, the term of this patent is extended or adjusted under 35 U.S.C. 154(b) by 1049 days.

(21) Appl. No.: 17/424,895

(22) PCT Filed: Jan. 30, 2020

(86) PCT No.: PCT/DK2020/050027
§ 371 (c)(1),
(2) Date: Jul. 22, 2021

(87) PCT Pub. No.: WO2020/156625
PCT Pub. Date: Aug. 6, 2020

(65) Prior Publication Data
US 2022/0087851 A1    Mar. 24, 2022

(30) Foreign Application Priority Data
Jan. 31, 2019    (DK) ............................ PA 2019 70070

(51) Int. Cl.
*A61F 5/443*    (2006.01)
*A61B 5/00*    (2006.01)
*A61F 5/44*    (2006.01)

(52) U.S. Cl.
CPC ............ *A61F 5/443* (2013.01); *A61B 5/6811* (2013.01); *A61B 5/6833* (2013.01); *A61F 5/4404* (2013.01)

(58) Field of Classification Search
CPC ............................ A61B 5/6811; A61B 5/6833
See application file for complete search history.

(56) References Cited

U.S. PATENT DOCUMENTS 2,327,514 A   8/1943   Fenwick
2,542,233 A   2/1951   Carroll
(Continued)

FOREIGN PATENT DOCUMENTS

AU   2007342523 B2   7/2011
CA      2540756 C    1/2008
(Continued)

*Primary Examiner* — Sarah Al Hashimi
*Assistant Examiner* — Hans Kaliher
(74) *Attorney, Agent, or Firm* — Coloplast Corp., Coloplast A/S; Nick Baumann

(57) ABSTRACT

Disclosed is a sensor patch (50) for attachment to a base plate for an ostomy appliance, and a method for manufacturing such sensor patch. The sensor patch having a proximal side and a distal side. The distal side being adapted for attachment to an adhesive surface of the base plate, wherein the adhesive surface of the base plate is adapted for attachment of the base plate to the skin surface of a user. The sensor patch comprises: a sensor assembly (204) comprising a plurality of electrodes (216), and a first adhesive sensor layer (52) forming the proximal side of the sensor patch and being adapted for attachment of the sensor patch to the skin surface of the user. The first adhesive sensor layer comprises a first centre portion (62) having a first centre thickness and a first outer rim portion (64) surrounding the first centre portion. The first outer rim portion has a first outer rim thickness decreasing along a radial direction from adjacent the first centre portion to a first outer periphery of the first adhesive sensor layer.

27 Claims, 5 Drawing Sheets

(56) References Cited

U.S. PATENT DOCUMENTS

| | | | |
|---|---|---|---|
| 2,544,579 A | 3/1951 | Ardner | |
| 3,214,502 A | 10/1965 | Schaar | |
| 3,808,354 A | 4/1974 | Feezor et al. | |
| 3,832,510 A | 8/1974 | Pfau et al. | |
| 3,915,171 A | 10/1975 | Shermeta | |
| 3,941,133 A | 3/1976 | Chen | |
| 4,231,369 A | 11/1980 | Sorensen et al. | |
| 4,372,308 A | 2/1983 | Steer et al. | |
| 4,449,970 A | 5/1984 | Bevan et al. | |
| 4,668,227 A | 5/1987 | Kay | |
| 4,754,264 A | 6/1988 | Okada et al. | |
| 4,775,374 A | 10/1988 | Cilento et al. | |
| 4,834,731 A | 5/1989 | Nowak et al. | |
| 4,973,323 A | 11/1990 | Kaczmarek et al. | |
| 4,982,742 A | 1/1991 | Claude | |
| 5,013,307 A | 5/1991 | Broida | |
| 5,016,645 A | 5/1991 | Williams et al. | |
| 5,051,259 A | 9/1991 | Olsen et al. | |
| 5,074,851 A | 12/1991 | Plass et al. | |
| 5,111,812 A | 5/1992 | Swanson et al. | |
| 5,147,343 A * | 9/1992 | Kellenberger | A61L 15/60 604/375 |
| 5,237,995 A | 8/1993 | Cano | |
| 5,318,543 A | 6/1994 | Ross et al. | |
| 5,322,797 A | 6/1994 | Mallow et al. | |
| 5,358,488 A | 10/1994 | Suriyapa | |
| 5,486,158 A | 1/1996 | Samuelsen | |
| 5,519,644 A | 5/1996 | Benton | |
| 5,570,082 A | 10/1996 | Mahgerefteh et al. | |
| 5,593,397 A | 1/1997 | La Gro | |
| 5,626,135 A | 5/1997 | Sanfilippo | |
| 5,672,163 A | 9/1997 | Ferreira et al. | |
| 5,677,221 A | 10/1997 | Tseng | |
| 5,704,905 A | 1/1998 | Jensen et al. | |
| 5,714,225 A | 2/1998 | Hansen et al. | |
| 5,790,036 A | 8/1998 | Fisher et al. | |
| 5,800,415 A | 9/1998 | Olsen | |
| 5,816,252 A | 10/1998 | Faries et al. | |
| 5,834,009 A | 11/1998 | Sawers et al. | |
| 5,846,558 A | 12/1998 | Nielsen et al. | |
| 5,876,855 A | 3/1999 | Wong et al. | |
| 5,879,292 A | 3/1999 | Sternberg et al. | |
| 5,942,186 A | 8/1999 | Sanada et al. | |
| 6,015,399 A | 1/2000 | Mracna et al. | |
| 6,025,725 A | 2/2000 | Gershenfeld et al. | |
| 6,078,261 A | 6/2000 | Davsko | |
| 6,093,276 A * | 7/2000 | Leise, Jr. | A61F 5/448 604/338 |
| 6,101,867 A | 8/2000 | Cavestri | |
| 6,103,033 A | 8/2000 | Say et al. | |
| 6,135,986 A | 10/2000 | Leisner et al. | |
| 6,171,289 B1 * | 1/2001 | Millot | A61F 5/443 604/336 |
| 6,206,864 B1 | 3/2001 | Kavanagh et al. | |
| 6,241,704 B1 | 6/2001 | Peterson et al. | |
| 6,270,445 B1 | 8/2001 | Dean, Jr. et al. | |
| 6,407,308 B1 | 6/2002 | Roe et al. | |
| 6,433,244 B1 | 8/2002 | Roe et al. | |
| 6,433,695 B1 | 8/2002 | Kai et al. | |
| 6,482,491 B1 | 11/2002 | Samuelsen et al. | |
| 6,485,476 B1 | 11/2002 | Von et al. | |
| 6,520,943 B1 | 2/2003 | Wagner | |
| 6,677,859 B1 | 1/2004 | Bensen | |
| 6,764,474 B2 | 7/2004 | Nielsen et al. | |
| 6,774,800 B2 | 8/2004 | Friedman et al. | |
| 7,014,816 B2 | 3/2006 | Miller et al. | |
| 7,066,919 B1 | 6/2006 | Sauerland et al. | |
| 7,150,728 B2 | 12/2006 | Hansen et al. | |
| 7,166,091 B1 | 1/2007 | Zeltner | |
| 7,199,501 B2 | 4/2007 | Pei et al. | |
| 7,214,217 B2 | 5/2007 | Pedersen et al. | |
| 7,326,190 B2 | 2/2008 | Botten | |
| 7,341,578 B2 | 3/2008 | Bulow et al. | |
| 7,347,844 B2 | 3/2008 | Cline et al. | |
| 7,367,965 B2 | 5/2008 | Poulsen et al. | |
| 7,559,922 B2 | 7/2009 | Botten | |
| 7,625,362 B2 | 12/2009 | Boehringer et al. | |
| 7,641,612 B1 | 1/2010 | McCall | |
| 7,670,289 B1 | 3/2010 | McCall | |
| 7,943,812 B2 | 5/2011 | Stroebeck et al. | |
| 7,981,098 B2 | 7/2011 | Boehringer et al. | |
| 8,061,360 B2 | 11/2011 | Locke et al. | |
| 8,277,427 B2 | 10/2012 | Edvardsen et al. | |
| 8,319,003 B2 | 11/2012 | Olsen et al. | |
| 8,326,051 B1 | 12/2012 | Hobbs | |
| 8,343,437 B2 | 1/2013 | Patel | |
| 8,398,575 B1 | 3/2013 | McCall | |
| 8,398,603 B2 | 3/2013 | Thirstrup et al. | |
| 8,399,732 B2 | 3/2013 | Oelund et al. | |
| 8,409,158 B2 | 4/2013 | Edvardsen et al. | |
| 8,439,883 B1 | 5/2013 | Johnsen | |
| 8,449,471 B2 | 5/2013 | Tran | |
| 8,500,718 B2 | 8/2013 | Locke et al. | |
| 8,507,081 B2 | 8/2013 | Strobech et al. | |
| 8,632,492 B2 | 1/2014 | Delegge | |
| 8,680,991 B2 | 3/2014 | Tran | |
| 8,684,982 B2 | 4/2014 | Nguyen-Demary et al. | |
| 8,707,766 B2 | 4/2014 | Harris et al. | |
| 8,740,865 B2 | 6/2014 | Krystek et al. | |
| 8,795,257 B2 | 8/2014 | Coulthard et al. | |
| 8,821,463 B2 | 9/2014 | Grum-Schwensen | |
| 8,821,464 B2 | 9/2014 | Hanuka et al. | |
| 8,975,465 B2 | 3/2015 | Hong et al. | |
| 8,978,452 B2 | 3/2015 | Johnson et al. | |
| 9,046,085 B2 | 6/2015 | Schoess et al. | |
| 9,066,812 B2 | 6/2015 | Edvardsen et al. | |
| 9,216,104 B2 | 12/2015 | Thirstrup et al. | |
| 9,308,332 B2 | 4/2016 | Heppe | |
| 9,322,797 B1 | 4/2016 | Lastinger et al. | |
| 9,506,886 B1 | 11/2016 | Woodbury et al. | |
| 9,566,383 B2 | 2/2017 | Yodfat et al. | |
| 9,629,964 B2 | 4/2017 | Wuepper | |
| 9,649,230 B1 | 5/2017 | Li | |
| 9,675,267 B2 | 6/2017 | Laakkonen et al. | |
| 9,693,908 B2 | 7/2017 | Eriksson et al. | |
| 9,770,359 B2 | 9/2017 | Edvardsen et al. | |
| 9,788,991 B2 | 10/2017 | Bird | |
| 9,867,934 B2 | 1/2018 | Heppe | |
| 9,928,341 B2 | 3/2018 | Angelides | |
| 10,016,298 B2 | 7/2018 | Thirstrup et al. | |
| 10,022,277 B2 | 7/2018 | Heil et al. | |
| D826,740 S | 8/2018 | Stevens et al. | |
| 10,426,342 B2 | 10/2019 | Hresko et al. | |
| 10,500,084 B2 | 12/2019 | Hansen et al. | |
| 10,531,977 B2 | 1/2020 | Schoess et al. | |
| 10,646,370 B2 | 5/2020 | Keleny et al. | |
| 10,792,184 B2 | 10/2020 | Hvid et al. | |
| 10,799,385 B2 | 10/2020 | Hansen et al. | |
| 10,849,781 B2 | 12/2020 | Hansen et al. | |
| 10,874,541 B2 | 12/2020 | Seres et al. | |
| 10,987,243 B2 | 4/2021 | Thirstrup et al. | |
| 11,096,818 B2 | 8/2021 | Thirstrup et al. | |
| 11,135,084 B2 | 10/2021 | Seres et al. | |
| 11,219,436 B2 | 1/2022 | Mayberg | |
| 11,238,133 B1 | 2/2022 | Brewer et al. | |
| 11,306,224 B2 | 4/2022 | Chatterjee et al. | |
| 11,406,525 B2 | 8/2022 | Seres et al. | |
| 11,471,318 B2 | 10/2022 | Hansen et al. | |
| 11,612,512 B2 | 3/2023 | Hansen et al. | |
| 11,903,728 B2 | 2/2024 | Svanegaard et al. | |
| 12,064,369 B2 | 8/2024 | Hansen et al. | |
| 2001/0041920 A1 | 11/2001 | Starkweather et al. | |
| 2001/0051787 A1 | 12/2001 | Haller et al. | |
| 2002/0013613 A1 | 1/2002 | Haller et al. | |
| 2002/0019615 A1 | 2/2002 | Roe et al. | |
| 2002/0109621 A1 | 8/2002 | Khair et al. | |
| 2003/0132763 A1 | 7/2003 | Ellenz | |
| 2003/0169032 A1 | 9/2003 | Minchole et al. | |
| 2004/0006320 A1 | 1/2004 | Buglino et al. | |
| 2004/0030305 A1 | 2/2004 | Sakamoto | |
| 2004/0036484 A1 | 2/2004 | Tamai | |
| 2004/0049145 A1 | 3/2004 | Flick | |
| 2004/0078219 A1 | 4/2004 | Kaylor et al. | |
| 2004/0100376 A1 | 5/2004 | Lye et al. | |

(56) References Cited

U.S. PATENT DOCUMENTS

| | | |
|---|---|---|
| 2004/0106908 A1 | 6/2004 | Leise et al. |
| 2004/0133175 A1 | 7/2004 | Hagedorn-Olsen |
| 2004/0171999 A1 | 9/2004 | Andersen et al. |
| 2004/0193122 A1 | 9/2004 | Cline et al. |
| 2004/0193123 A1 | 9/2004 | Fenton |
| 2004/0216833 A1 | 11/2004 | Fleming et al. |
| 2005/0038325 A1 | 2/2005 | Moll |
| 2005/0054997 A1 | 3/2005 | Buglino et al. |
| 2005/0065488 A1 | 3/2005 | Elliott |
| 2005/0070863 A1 | 3/2005 | Bulow et al. |
| 2005/0085779 A1 | 4/2005 | Poulsen et al. |
| 2005/0101841 A9 | 5/2005 | Kaylor et al. |
| 2005/0240163 A1 | 10/2005 | Andersen |
| 2005/0256545 A1 | 11/2005 | Koh et al. |
| 2005/0261645 A1 | 11/2005 | Conrad et al. |
| 2006/0015081 A1 | 1/2006 | Suzuki et al. |
| 2006/0025727 A1 | 2/2006 | Boehringer et al. |
| 2006/0052752 A1 | 3/2006 | McMichael |
| 2006/0194324 A1 | 8/2006 | Faries et al. |
| 2006/0271002 A1 | 11/2006 | Botten |
| 2007/0035405 A1 | 2/2007 | Wada et al. |
| 2007/0135782 A1 | 6/2007 | Bager et al. |
| 2007/0185464 A1 | 8/2007 | Fattman et al. |
| 2007/0203407 A1 | 8/2007 | Hoss et al. |
| 2007/0204691 A1 | 9/2007 | Bogner et al. |
| 2008/0004580 A1 | 1/2008 | Mullejans et al. |
| 2008/0038536 A1 | 2/2008 | Strobech et al. |
| 2008/0041792 A1 | 2/2008 | Crnkovich et al. |
| 2008/0058740 A1 | 3/2008 | Sullivan et al. |
| 2008/0061965 A1 | 3/2008 | Kuhns et al. |
| 2008/0071214 A1 | 3/2008 | Locke et al. |
| 2008/0075934 A1 | 3/2008 | Barlow et al. |
| 2008/0091154 A1 | 4/2008 | Botten |
| 2008/0140057 A1 | 6/2008 | Wood et al. |
| 2008/0234641 A1 | 9/2008 | Locke et al. |
| 2008/0255808 A1 | 10/2008 | Hayter |
| 2008/0275327 A1 | 11/2008 | Faarbaek et al. |
| 2008/0278337 A1 | 11/2008 | Huang et al. |
| 2008/0300559 A1 | 12/2008 | Gustafson et al. |
| 2008/0300578 A1 | 12/2008 | Freedman |
| 2008/0306459 A1 | 12/2008 | Albrectsen |
| 2009/0012501 A1 | 1/2009 | Boehringer et al. |
| 2009/0118687 A1 | 5/2009 | Kristensen et al. |
| 2009/0167286 A1 | 7/2009 | Naylor et al. |
| 2009/0173935 A1 | 7/2009 | Cho et al. |
| 2009/0227969 A1 | 9/2009 | Jaeb et al. |
| 2009/0234916 A1 | 9/2009 | Cosentino et al. |
| 2009/0247970 A1 | 10/2009 | Keleny et al. |
| 2009/0264957 A1 | 10/2009 | Giftakis et al. |
| 2010/0010460 A1 | 1/2010 | Butler |
| 2010/0030167 A1 | 2/2010 | Thirstrup et al. |
| 2010/0072271 A1 | 3/2010 | Thorstensson |
| 2010/0106220 A1 | 4/2010 | Ecker et al. |
| 2010/0114047 A1 | 5/2010 | Song et al. |
| 2010/0191201 A1* | 7/2010 | Bach .................. A61L 24/0031 604/336 |
| 2010/0271212 A1 | 10/2010 | Page |
| 2010/0311167 A1 | 12/2010 | Wood et al. |
| 2011/0034890 A1 | 2/2011 | Stroebech et al. |
| 2011/0071482 A1 | 3/2011 | Selevan |
| 2011/0077497 A1 | 3/2011 | Oster et al. |
| 2011/0130642 A1 | 6/2011 | Jaeb et al. |
| 2011/0144470 A1 | 6/2011 | Mazar et al. |
| 2011/0191044 A1 | 8/2011 | Stafford |
| 2011/0245682 A1 | 10/2011 | Robinson et al. |
| 2011/0246983 A1 | 10/2011 | Brunet et al. |
| 2011/0257496 A1 | 10/2011 | Terashima et al. |
| 2012/0013130 A1 | 1/2012 | Jung |
| 2012/0089037 A1 | 4/2012 | Bishay et al. |
| 2012/0143154 A1 | 6/2012 | Edvardsen et al. |
| 2012/0143155 A1 | 6/2012 | Edvardsen et al. |
| 2012/0258302 A1 | 10/2012 | Hunt et al. |
| 2012/0283678 A1 | 11/2012 | Nguyen-Demary et al. |
| 2012/0304767 A1 | 12/2012 | Howard et al. |
| 2012/0323086 A1 | 12/2012 | Hansen |
| 2013/0018231 A1 | 1/2013 | Hong et al. |
| 2013/0030167 A1 | 1/2013 | Wang et al. |
| 2013/0030397 A1 | 1/2013 | Sabeti |
| 2013/0060213 A1 | 3/2013 | Hanuka et al. |
| 2013/0066285 A1 | 3/2013 | Locke et al. |
| 2013/0072886 A1 | 3/2013 | Schertiger et al. |
| 2013/0078912 A1 | 3/2013 | San Vicente et al. |
| 2013/0086217 A1 | 4/2013 | Price et al. |
| 2013/0102979 A1 | 4/2013 | Coulthard et al. |
| 2013/0138065 A1 | 5/2013 | Buus |
| 2013/0150769 A1 | 6/2013 | Heppe |
| 2013/0165862 A1 | 6/2013 | Griffith et al. |
| 2013/0192604 A1 | 8/2013 | Persson et al. |
| 2013/0226116 A1 | 8/2013 | Edvardsen et al. |
| 2013/0231620 A1 | 9/2013 | Thirstrup et al. |
| 2013/0254141 A1 | 9/2013 | Barda et al. |
| 2013/0303867 A1 | 11/2013 | Elfstrom et al. |
| 2013/0307570 A1 | 11/2013 | Bosaeus et al. |
| 2013/0324952 A1 | 12/2013 | Krystek et al. |
| 2013/0324955 A1 | 12/2013 | Wong et al. |
| 2013/0332085 A1 | 12/2013 | Yang et al. |
| 2014/0051946 A1 | 2/2014 | Arne et al. |
| 2014/0128815 A1 | 5/2014 | Cabiri et al. |
| 2014/0200426 A1 | 7/2014 | Taub et al. |
| 2014/0200538 A1 | 7/2014 | Euliano et al. |
| 2014/0236111 A1 | 8/2014 | Casado et al. |
| 2014/0275854 A1 | 9/2014 | Venkatraman et al. |
| 2014/0276501 A1 | 9/2014 | Cisko |
| 2014/0288381 A1 | 9/2014 | Faarbaek et al. |
| 2014/0309600 A1 | 10/2014 | Aceto et al. |
| 2014/0323909 A1 | 10/2014 | Kim |
| 2014/0327433 A1 | 11/2014 | Anway et al. |
| 2014/0336493 A1 | 11/2014 | Kulach et al. |
| 2015/0057634 A1 | 2/2015 | Mastrototaro et al. |
| 2015/0150457 A1 | 6/2015 | Wu et al. |
| 2015/0151051 A1 | 6/2015 | Tsoukalis |
| 2015/0230706 A1 | 8/2015 | Nakagawa et al. |
| 2015/0231802 A1 | 8/2015 | Quan et al. |
| 2015/0250639 A1 | 9/2015 | Thirstrup et al. |
| 2015/0257923 A1 | 9/2015 | Thirstrup et al. |
| 2015/0272495 A1 | 10/2015 | Greener |
| 2015/0328389 A1 | 11/2015 | Heppe |
| 2015/0342777 A1 | 12/2015 | Seres et al. |
| 2015/0374896 A1 | 12/2015 | Du et al. |
| 2016/0008182 A1 | 1/2016 | Prokopuk et al. |
| 2016/0058604 A1 | 3/2016 | Wiltshire et al. |
| 2016/0084869 A1 | 3/2016 | Yuen et al. |
| 2016/0103966 A1 | 4/2016 | Mirza |
| 2016/0117062 A1 | 4/2016 | Hussam et al. |
| 2016/0158056 A1 | 6/2016 | Davis et al. |
| 2016/0158517 A1 | 6/2016 | Nebbia |
| 2016/0158969 A1 | 6/2016 | McLane et al. |
| 2016/0166438 A1 | 6/2016 | Rovaniemi |
| 2016/0178387 A1 | 6/2016 | Yamasaki et al. |
| 2016/0198996 A1 | 7/2016 | Dullen |
| 2016/0218555 A1 | 7/2016 | Slaby et al. |
| 2016/0235581 A1 | 8/2016 | Keleny et al. |
| 2016/0235582 A1 | 8/2016 | Moavenian |
| 2016/0242654 A1 | 8/2016 | Quinlan et al. |
| 2016/0267769 A1 | 9/2016 | Rokhsaz et al. |
| 2016/0278990 A1 | 9/2016 | Chen |
| 2016/0305776 A1 | 10/2016 | Mrtensson et al. |
| 2016/0310077 A1 | 10/2016 | Hunter et al. |
| 2016/0310140 A1 | 10/2016 | Belson et al. |
| 2016/0310329 A1 | 10/2016 | Patel et al. |
| 2016/0331232 A1 | 11/2016 | Love et al. |
| 2016/0331235 A1 | 11/2016 | Nyberg et al. |
| 2016/0361015 A1 | 12/2016 | Wang et al. |
| 2017/0042614 A1 | 2/2017 | Salahieh et al. |
| 2017/0050004 A1 | 2/2017 | Tilson et al. |
| 2017/0055896 A1 | 3/2017 | Al-Ali et al. |
| 2017/0090236 A1 | 3/2017 | Yeh et al. |
| 2017/0098044 A1 | 4/2017 | Lai et al. |
| 2017/0113001 A1 | 4/2017 | Trock |
| 2017/0140103 A1 | 5/2017 | Angelides |
| 2017/0156920 A1 | 6/2017 | Hunt et al. |
| 2017/0181628 A1 | 6/2017 | Burnette et al. |
| 2017/0340474 A1 | 11/2017 | Thirstrup et al. |
| 2017/0340498 A1 | 11/2017 | Tessmer et al. |

(56) References Cited

U.S. PATENT DOCUMENTS

| | | |
|---|---|---|
| 2017/0348137 A1 | 12/2017 | Hvid et al. |
| 2017/0348162 A1 | 12/2017 | Arizti et al. |
| 2017/0360592 A1 | 12/2017 | Carrubba |
| 2017/0360593 A1 | 12/2017 | Cox |
| 2018/0049667 A1 | 2/2018 | Heppe |
| 2018/0055359 A1 | 3/2018 | Shamim et al. |
| 2018/0110078 A1 | 4/2018 | Mandapaka et al. |
| 2018/0136712 A1 | 5/2018 | Niikura et al. |
| 2018/0171183 A1 | 6/2018 | Sakurai et al. |
| 2018/0298240 A1 | 10/2018 | Chatterjee et al. |
| 2018/0318475 A1 | 11/2018 | Thomson et al. |
| 2019/0008439 A1 | 1/2019 | Sageder et al. |
| 2019/0133810 A1 | 5/2019 | Seres et al. |
| 2019/0133811 A1 | 5/2019 | Seres et al. |
| 2019/0133812 A1 | 5/2019 | Seres et al. |
| 2019/0142623 A1 | 5/2019 | Schoess et al. |
| 2019/0175386 A1 | 6/2019 | Monty |
| 2019/0184093 A1 | 6/2019 | Sjolund et al. |
| 2019/0192066 A1 | 6/2019 | Schoess et al. |
| 2019/0192332 A1 | 6/2019 | Hansen et al. |
| 2019/0192333 A1 | 6/2019 | Hansen et al. |
| 2019/0192334 A1 | 6/2019 | Hansen et al. |
| 2019/0240059 A1 | 8/2019 | Seres et al. |
| 2019/0247050 A1 | 8/2019 | Goldsmith |
| 2019/0252079 A1 | 8/2019 | Constantin et al. |
| 2019/0374163 A1 | 12/2019 | Faarbaek et al. |
| 2020/0000624 A1 | 1/2020 | Gibbons et al. |
| 2020/0078206 A1 | 3/2020 | Chiladakis |
| 2020/0100931 A1 | 4/2020 | Schoess et al. |
| 2020/0114535 A1 | 4/2020 | Wattam et al. |
| 2020/0188161 A1 | 6/2020 | Seres et al. |
| 2020/0246174 A1 | 8/2020 | Hansen et al. |
| 2020/0246175 A1 | 8/2020 | Hansen et al. |
| 2020/0246176 A1 | 8/2020 | Hansen et al. |
| 2020/0246177 A1 | 8/2020 | Hansen et al. |
| 2020/0276063 A1 | 9/2020 | Munoz Herencia |
| 2020/0279368 A1 | 9/2020 | Tada et al. |
| 2020/0297244 A1 | 9/2020 | Brownhill et al. |
| 2020/0306074 A1 | 10/2020 | Speiermann et al. |
| 2020/0322793 A1 | 10/2020 | Yang |
| 2020/0330258 A1 | 10/2020 | Hansen et al. |
| 2020/0330260 A1 | 10/2020 | Hansen et al. |
| 2020/0337880 A1 | 10/2020 | Hansen et al. |
| 2020/0337881 A1 | 10/2020 | Hansen et al. |
| 2020/0337882 A1 | 10/2020 | Hansen et al. |
| 2020/0337883 A1 | 10/2020 | Hansen et al. |
| 2020/0375499 A1 | 12/2020 | Hansen et al. |
| 2020/0375782 A1 | 12/2020 | Hansen et al. |
| 2020/0375783 A1 | 12/2020 | Hansen et al. |
| 2020/0375784 A1 | 12/2020 | Hansen et al. |
| 2020/0375785 A1 | 12/2020 | Hansen et al. |
| 2020/0375786 A1 | 12/2020 | Hansen et al. |
| 2020/0375809 A1 | 12/2020 | Sullivan et al. |
| 2020/0383637 A1 | 12/2020 | Hansen et al. |
| 2020/0383818 A1 | 12/2020 | Hansen et al. |
| 2020/0383819 A1 | 12/2020 | Sletten et al. |
| 2020/0383820 A1 | 12/2020 | Hansen et al. |
| 2020/0383821 A1 | 12/2020 | Hansen et al. |
| 2020/0390587 A1 | 12/2020 | Svanegaard et al. |
| 2020/0390588 A1 | 12/2020 | Hansen et al. |
| 2020/0390589 A1 | 12/2020 | Hansen et al. |
| 2020/0395120 A1 | 12/2020 | Svanegaard et al. |
| 2020/0395610 A1 | 12/2020 | Ono et al. |
| 2020/0405228 A1 | 12/2020 | Svanegaard et al. |
| 2020/0405229 A1 | 12/2020 | Svanegaard et al. |
| 2020/0405230 A1 | 12/2020 | Svanegaard et al. |
| 2021/0000414 A1 | 1/2021 | Svanegaard et al. |
| 2021/0000633 A1 | 1/2021 | Hansen et al. |
| 2021/0000634 A1 | 1/2021 | Svanegaard et al. |
| 2021/0000635 A1 | 1/2021 | Hansen et al. |
| 2021/0000636 A1 | 1/2021 | Hansen et al. |
| 2021/0007663 A1 | 1/2021 | Svanegaard et al. |
| 2021/0007881 A1 | 1/2021 | Svanegaard et al. |
| 2021/0015653 A1 | 1/2021 | Hansen et al. |
| 2021/0015654 A1 | 1/2021 | Hansen et al. |
| 2021/0022683 A1 | 1/2021 | Faarbaek et al. |
| 2021/0038424 A1 | 2/2021 | Svanegaard et al. |
| 2021/0059603 A1 | 3/2021 | Svanegaard et al. |
| 2021/0085511 A1 | 3/2021 | Hansen et al. |
| 2021/0085512 A1 | 3/2021 | Hansen et al. |
| 2021/0100533 A1 | 4/2021 | Seres et al. |
| 2021/0128364 A1 | 5/2021 | Cole et al. |
| 2021/0145354 A1 | 5/2021 | Hunt et al. |
| 2021/0177642 A1 | 6/2021 | Andersen et al. |
| 2021/0212855 A1 | 7/2021 | Hansen et al. |
| 2021/0228194 A1 | 7/2021 | Mayberg |
| 2021/0338471 A1 | 11/2021 | Nolan et al. |
| 2021/0361464 A1 | 11/2021 | Larsen et al. |
| 2021/0361465 A1 | 11/2021 | Hansen et al. |
| 2021/0361466 A1 | 11/2021 | Hansen et al. |
| 2021/0361467 A1 | 11/2021 | Hansen et al. |
| 2021/0369197 A1 | 12/2021 | Hansen et al. |
| 2021/0369488 A1 | 12/2021 | Hansen et al. |
| 2021/0369489 A1 | 12/2021 | Hansen et al. |
| 2021/0369490 A1 | 12/2021 | Hansen et al. |
| 2021/0370217 A1 | 12/2021 | Kirschman |
| 2021/0386368 A1 | 12/2021 | Carlsson et al. |
| 2022/0000652 A1 | 1/2022 | Thirstrup et al. |
| 2022/0031227 A1 | 2/2022 | Cho et al. |
| 2022/0031495 A1 | 2/2022 | Seres et al. |
| 2022/0079802 A1 | 3/2022 | Hansen |
| 2022/0079803 A1 | 3/2022 | Windeballe et al. |
| 2022/0087851 A1 | 3/2022 | Stroebech |
| 2022/0110585 A1 | 4/2022 | Andersen |
| 2022/0117771 A1 | 4/2022 | Fearn et al. |
| 2022/0142807 A1 | 5/2022 | Tofte |
| 2022/0192860 A1 | 6/2022 | Hansen et al. |
| 2022/0241104 A1 | 8/2022 | Knoedler |
| 2022/0241105 A1 | 8/2022 | Hansen et al. |
| 2022/0265458 A1 | 8/2022 | Carlsson et al. |
| 2022/0304844 A1 | 9/2022 | Carlsson et al. |
| 2023/0059470 A1 | 2/2023 | Hansen et al. |
| 2023/0064734 A1 | 3/2023 | Hansen et al. |
| 2023/0105402 A1 | 4/2023 | Hansen et al. |
| 2023/0117727 A1 | 4/2023 | Hansen et al. |
| 2023/0118594 A1 | 4/2023 | Speiermann et al. |
| 2023/0141297 A1 | 5/2023 | Herold et al. |
| 2023/0141719 A1 | 5/2023 | Emborg et al. |
| 2023/0142141 A1 | 5/2023 | Emborg et al. |
| 2023/0145670 A1 | 5/2023 | Seres et al. |
| 2023/0146436 A1 | 5/2023 | Hansen et al. |
| 2023/0147665 A1 | 5/2023 | Hasbeck et al. |
| 2023/0190509 A1 | 6/2023 | Hansen et al. |
| 2023/0210682 A1 | 7/2023 | Hansen et al. |
| 2023/0233147 A1 | 7/2023 | Hansen et al. |
| 2023/0255811 A1 | 8/2023 | Carlsson et al. |
| 2023/0284932 A1 | 9/2023 | Hansen et al. |
| 2023/0293333 A1 | 9/2023 | Hansen et al. |
| 2023/0293335 A1 | 9/2023 | Hansen et al. |
| 2023/0301818 A1 | 9/2023 | Hansen et al. |
| 2023/0310201 A1 | 10/2023 | Hansen et al. |
| 2023/0329893 A1 | 10/2023 | Olsen et al. |
| 2023/0338005 A1 | 10/2023 | Barthe et al. |
| 2023/0372141 A1 | 11/2023 | Larsen et al. |
| 2023/0414397 A1 | 12/2023 | Hansen et al. |
| 2024/0009020 A1 | 1/2024 | Hansen et al. |
| 2024/0041635 A1 | 2/2024 | Hansen et al. |
| 2024/0180740 A1 | 6/2024 | Hansen et al. |
| 2024/0225539 A1 | 7/2024 | Svanegaard et al. |
| 2024/0261130 A1 | 8/2024 | Hansen et al. |

FOREIGN PATENT DOCUMENTS

| | | |
|---|---|---|
| CA | 3009449 C | 9/2019 |
| CA | 3002372 C | 3/2021 |
| CA | 2947016 C | 2/2023 |
| CN | 103269668 A | 8/2013 |
| CN | 203786580 U | 8/2014 |
| CN | 104902399 A | 9/2015 |
| CN | 104980878 A | 10/2015 |
| CN | 105588856 A | 5/2016 |
| CN | 106062546 A | 10/2016 |
| CN | 206271160 U | 6/2017 |
| CN | 206450708 U | 8/2017 |

(56) References Cited

FOREIGN PATENT DOCUMENTS

| | | |
|---|---|---|
| CN | 105615896 B | 5/2019 |
| CN | 105359167 B | 6/2019 |
| DE | 3437950 A1 | 4/1985 |
| DE | 3836590 A1 | 5/1990 |
| DE | 19953062 A1 | 5/2000 |
| DE | 19900611 C1 | 7/2000 |
| DE | 102011014321 A1 | 9/2012 |
| DE | 102011076219 A1 | 11/2012 |
| EP | 0168967 A1 | 1/1986 |
| EP | 0373782 A1 | 6/1990 |
| EP | 0416397 A1 | 3/1991 |
| EP | 0850076 B1 | 4/2005 |
| EP | 1188157 B1 | 12/2005 |
| EP | 2108345 A1 | 10/2009 |
| EP | 2489561 A2 | 8/2012 |
| EP | 2654646 A2 | 10/2013 |
| EP | 2453851 B1 | 10/2014 |
| EP | 3064179 A1 | 9/2016 |
| EP | 3213727 A1 | 9/2017 |
| GB | 2219679 A | 12/1989 |
| GB | 2225951 A | 6/1990 |
| GB | 2343628 A | 5/2000 |
| GB | 2465742 A | 6/2010 |
| GB | 2542093 A | 3/2017 |
| JP | 04-074882 A | 3/1992 |
| JP | 06-152077 A | 5/1994 |
| JP | 09-010184 A | 1/1997 |
| JP | 11-128352 A | 5/1999 |
| JP | 2000-093448 A | 4/2000 |
| JP | 2001-087299 A | 4/2001 |
| JP | 2002-055074 A | 2/2002 |
| JP | 2002-224093 A | 8/2002 |
| JP | 2005-323981 A | 11/2005 |
| JP | 2007-319561 A | 12/2007 |
| JP | 2014-033745 A | 2/2014 |
| JP | 2014-054368 A | 3/2014 |
| JP | 2014-507182 A | 3/2014 |
| JP | 2014151096 A | 8/2014 |
| KR | 10-2012-0003987 A | 1/2012 |
| NL | 1003904 C2 | 3/1998 |
| RU | 2527155 C2 | 8/2014 |
| TW | 201201783 A | 1/2012 |
| WO | 94/15562 A1 | 7/1994 |
| WO | 97/10012 A1 | 3/1997 |
| WO | 99/33037 A1 | 7/1999 |
| WO | 99/36017 A1 | 7/1999 |
| WO | 00/79497 A1 | 12/2000 |
| WO | 01/13830 A1 | 3/2001 |
| WO | 01/50996 A1 | 7/2001 |
| WO | 02/52302 A2 | 7/2002 |
| WO | 02/99765 A1 | 12/2002 |
| WO | WO-2004084778 A2 * | 10/2004 ............. A61F 5/443 |
| WO | 2005/038693 A1 | 4/2005 |
| WO | 2005/082271 A2 | 9/2005 |
| WO | 2006/008866 A1 | 1/2006 |
| WO | 2006/094513 A2 | 9/2006 |
| WO | 2007/000168 A1 | 1/2007 |
| WO | 2007/059774 A2 | 5/2007 |
| WO | 2007/070266 A1 | 6/2007 |
| WO | 2007/098762 A1 | 9/2007 |
| WO | 2007/133555 A2 | 11/2007 |
| WO | 2007128038 A1 | 11/2007 |
| WO | 2008/057884 A2 | 5/2008 |
| WO | 2009/006900 A1 | 1/2009 |
| WO | 2009/052496 A1 | 4/2009 |
| WO | 2009/107011 A1 | 9/2009 |
| WO | 2009/112912 A2 | 9/2009 |
| WO | 2011/003421 A1 | 1/2011 |
| WO | 2011/004165 A1 | 1/2011 |
| WO | 2011003420 A1 | 1/2011 |
| WO | 2011/061540 A1 | 5/2011 |
| WO | 2011/105701 A2 | 9/2011 |
| WO | 2011/123018 A1 | 10/2011 |
| WO | 2011/139499 A1 | 11/2011 |
| WO | 2011/161254 A2 | 12/2011 |
| WO | 2012/068386 A1 | 5/2012 |
| WO | 2012/076022 A2 | 6/2012 |
| WO | 2012/084987 A2 | 6/2012 |
| WO | 2013/013197 A1 | 1/2013 |
| WO | 2013095231 A1 | 6/2013 |
| WO | 2013164517 A1 | 11/2013 |
| WO | 2014/004207 A1 | 1/2014 |
| WO | 2014/086369 A1 | 6/2014 |
| WO | 2014116816 A1 | 7/2014 |
| WO | 2015/007284 A1 | 1/2015 |
| WO | 2015/014774 A1 | 2/2015 |
| WO | 2015/084462 A1 | 6/2015 |
| WO | 2015/094064 A1 | 6/2015 |
| WO | 2015/187366 A1 | 12/2015 |
| WO | 2015186452 A1 | 12/2015 |
| WO | 2016/132738 A1 | 8/2016 |
| WO | 2016124202 A1 | 8/2016 |
| WO | 2016/166731 A1 | 10/2016 |
| WO | 2016162038 A1 | 10/2016 |
| WO | 2016/192738 A1 | 12/2016 |
| WO | 2017/023794 A1 | 2/2017 |
| WO | 2017/062042 A1 | 4/2017 |
| WO | 2017/067558 A1 | 4/2017 |
| WO | 2017/067560 A1 | 4/2017 |
| WO | 2017/074505 A1 | 5/2017 |
| WO | 2017/088153 A1 | 6/2017 |
| WO | 2017108109 A1 | 6/2017 |
| WO | 2017/136696 A1 | 8/2017 |
| WO | 2017/190752 A1 | 11/2017 |
| WO | 2018/028756 A1 | 2/2018 |
| WO | 2019/094635 A1 | 5/2019 |
| WO | 2019/120432 A1 | 6/2019 |
| WO | 2019/161859 A1 | 8/2019 |
| WO | 2019/161860 A1 | 8/2019 |
| WO | 2019/161863 A1 | 8/2019 |
| WO | 2019/174693 A1 | 9/2019 |
| WO | 2019/174695 A1 | 9/2019 |
| WO | 2019/213623 A1 | 11/2019 |
| WO | 2020/035121 A1 | 2/2020 |

\* cited by examiner

STOMAL SENSOR PATCH

The present disclosure relates to a sensor patch for attachment to base plate for an ostomy appliance. In particular the present disclosure relates to the thickness of such a sensor patch.

BACKGROUND

Stomal output often contains body fluids and visceral contents that are aggressive to both the skin of a user and to ostomy devices, these have a detrimental effect on the efficiency and integrity of the adhesive materials that are applied to attach the ostomy device to the user's skin surface. For users in general safe, reliable and efficient ostomy devices are evidently highly desirable.

However, a particularly major and persistent concern of a large population of ostomists continues to be failure of the base plate adhesive attaching the ostomy appliance to the user's skin surface, because such failure almost inevitably leads to embarrassing and stigmatising leakage incidents. Such incidents in turn are known from several user interviews to lead to a reduced quality-of-life feeling. Adhesive failure of the base plate adhesive can result from various reasons. Most often, a leakage incident is caused by stomal output entering between the proximal surface of the base plate and the user's skin, e.g. due to less-than-optimal attachment of the base plate to the skin arising from e.g. uneven skin surface or skin folds. This undesirable progression of stomal output "underneath" the adhesive leads to deterioration and/or weakening of the adhesive material carrying the weight and providing the seal of the ostomy appliance. Often such failure happens surprisingly fast and is only detectable for the user once the failure has already become so severe that leakage occurs, requiring immediate change of the ostomy appliance and possibly also of the user's clothes.

In other instances, the primary factor of adhesive failure is simply a question of how much time has elapsed since the base plate of the ostomy appliance was first applied to the user's skin surface. In addition to the output from the stoma itself, the peristomal skin surface continuously secretes some moisture (e.g. sweat). To mitigate this, most often adhesives of base plates for ostomy devices include hydrocolloid materials which are capable of absorbing high levels of moisture, thereby stabilizing the polymer matrix of the adhesive material and prolonging the lifetime ("wear time") of the base plate. However, eventually the adhesion capability of the base plate no longer can support the force exerted on the base plate from the load of the output collecting bag, and the appliance must be replaced.

As there can be considerable differences in the severity and/or speed by which adhesive failure and potentially leakage occur, which differences at least to some extent are correlated to various factors including those presented above, a mere indication that failure or leakage is imminent, or that it has already occurred, fails to represent a reliable and satisfactory solution to the problem of avoiding sudden embarrassing and stigmatising leakage incidents in ostomy appliances. In other words, the users of ostomy appliances could greatly benefit from an appliance solution which provides them with better guidance and options regarding how and—not least—how quickly to react to beginning failure or leakage of the adhesive of the base plate of the appliance. More generally, ostomists and health care professionals alike would welcome improvements in ostomy devices to reduce or eliminate the occurrence of sudden leakage incidents.

SUMMARY

It is an object of the present disclosure to provide a sensor patch and a base plate for facilitating reliable and/or improved detection of risk of failure of an ostomy appliance and/or improved detection of risk of leakage. The disclosed sensor patch and base plate may be provided to facilitate detection of risk of failure and/or risk of leakage with respect to an adhesive base plate of the ostomy appliance.

It is a further object of the present disclosure to provide ways of facilitating attachment of a sensor patch to an ostomy appliance, such as a base plate of the ostomy appliance, which reduces the risk of compromising the capability of the ostomy appliance to avoid leakage, in particular between the skin surface of the user and the adhesive surface of the base plate. In particular, it is an object of the present disclosure to reduce the edge of the sensor patch, such that a transition from the adhesive surface of a base plate to the adhesive surface of the sensor patch attached to the adhesive surface of the base plate is a smooth as possible. In other words, it is an object of the present disclosure to reduce the edge formed between the adhesive surface of the base plate and the sensor patch attached thereto. In particular, it is envisioned that the presence of such an edge may cause unfavourable effects to the quality of adhesion of the base plate/sensor patch to the skin surface of the user, and as such, it is an object to reduce such an edge.

Thus, the present disclosure relates to a sensor patch and a method for manufacturing a sensor patch. Also, the present disclosure relates to a base plate for an ostomy appliance.

Accordingly, a sensor patch for attachment to a base plate for an ostomy appliance is disclosed. The sensor patch has a proximal side and a distal side. The distal side is adapted for attachment to an adhesive surface of the base plate, wherein the adhesive surface of the base plate is adapted for attachment of the base plate to the skin surface of a user.

The sensor patch comprises: a sensor assembly comprising a plurality of electrodes including a first electrode and a second electrode for forming a first sensor; and a first adhesive sensor layer forming the proximal side of the sensor patch and being adapted for attachment of the sensor patch to the skin surface of the user. The first adhesive sensor layer comprises a first centre portion having a first centre thickness and a first outer rim portion surrounding the first centre portion. The first outer rim portion has a first outer rim thickness decreasing along a radial direction from adjacent the first centre portion to a first outer periphery of the first adhesive sensor layer. The first outer rim thickness adjacent the centre portion is the first centre thickness and the first outer rim thickness at the first outer periphery of the first adhesive sensor layer is a first minimum outer rim thickness.

The sensor patch is adapted to form a stomal opening with a centre point. The stomal opening is configured to allow passage of output through the stomal opening and into an ostomy pouch attached to the base plate.

Thereby is provided a sensor patch having a chamfered edge, whereby the transition between a base plate and the sensor patch attached to the base plate is smoothed. The sensor patch having the chamfered edge may reduce the potentially unfavourable effects of having a sensor patch attached to the adhesive surface of a base plate, such as the effects the attached sensor patch may have on the quality of adhesion to the skin surface.

Also disclosed is a method for manufacturing a sensor patch, such as the above-disclosed sensor patch, such as a sensor patch having a proximal side and a distal side and being adapted for attachment of the distal side to an adhesive surface of a base plate for an ostomy appliance wherein the adhesive surface of the base plate is adapted for attachment of the base plate to the skin surface of a user.

The method comprises providing a first adhesive sensor material and laying out a layer of the first adhesive sensor material for forming a first adhesive sensor layer of the sensor patch, wherein the first adhesive sensor material is laid out to form a first centre portion and a first outer rim portion surrounding the first centre portion, wherein the first centre portion has a first centre thickness and the first outer rim portion has a first outer rim thickness gradually decreasing along a radial direction from adjacent the first centre portion to the first outer periphery of the first adhesive sensor layer, and wherein the first outer rim thickness adjacent the first centre portion is the first centre thickness and the first outer rim thickness at the first outer periphery of the first adhesive sensor layer is a first minimum outer rim thickness.

The method comprises providing a sensor assembly comprising a plurality of electrodes including a first electrode and a second electrode for forming a first sensor.

The method comprises arranging the sensor assembly on a distal side of the first adhesive sensor layer, wherein a proximal side of the first adhesive sensor layer is adapted for attachment of the sensor patch to the skin surface of the user.

Thereby is provided a method for manufacturing a sensor patch having a chamfered edge facilitating that the transition between a base plate and the sensor patch attached to the base plate is smoothed.

Also disclosed is a base plate for an ostomy appliance having a proximal adhesive surface adapted for attachment of the base plate to the skin surface of a user.

BRIEF DESCRIPTION OF THE FIGURES

Embodiments of the disclosure will be described in more detail in the following with regard to the accompanying figures. The figures show one way of implementing the present invention and are not to be construed as being limiting to other possible embodiments falling within the scope of the attached claim set.

DETAILED DESCRIPTION

Figure 1:
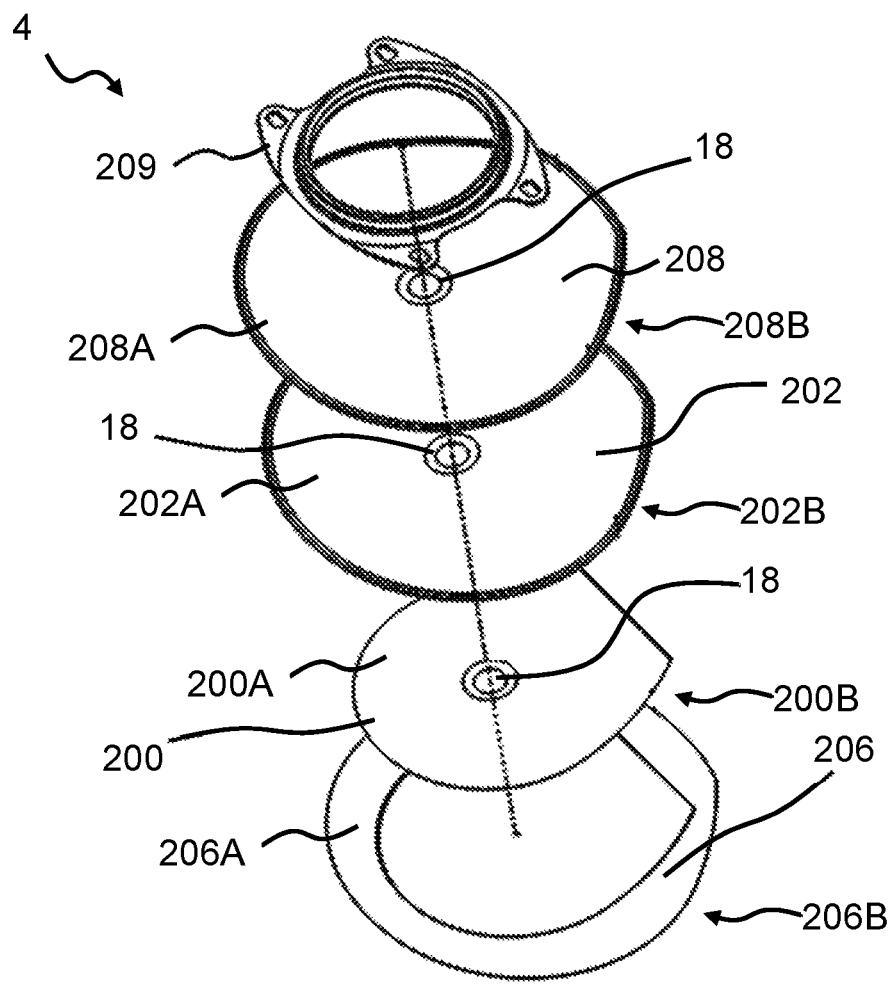
FIG. 1 schematically illustrates an exploded view of an exemplary base plate, FIG. 2 schematically illustrates an exploded view of an exemplary sensor patch, FIG. 3 schematically illustrates an exemplary electrode configuration, FIG. 4 schematically illustrates a cross section of a sensor patch.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with respect to the orientation of the Figure(s) being described. Because components of embodiments can be positioned in a number of different orientations, the directional terminology is used for purposes of illustration and is in no way limiting. It is to be understood that other embodiments may be utilized, and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side of a device or part of a device, the referral is to the skin-facing side, when the ostomy appliance is worn by a user. Likewise, whenever referring to the distal side of a device or part of a device, the referral is to the side facing away from the skin, when the ostomy appliance is worn by a user. In other words, the proximal side is the side closest to the user, when the appliance is fitted on a user and the distal side is the opposite side—the side furthest away from the user in use.

The axial direction is defined as the direction of the stoma, when the appliance is worn by a user. Thus, the axial direction is generally perpendicular to the skin or abdominal surface of the user.

The radial direction is defined as transverse to the axial direction that is transversely to the direction of the stoma, i.e. "across" the distal/proximal surface of the base plate. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The use of the word "essentially" as a qualifier to certain structural and functional features or effects in this disclosure is used for emphasizing what is the most important focus of something or fact about something (i.e. a feature may have or fulfil a variety of effects, but when the disclosure discusses one effect as being "essentially" provided, this is the focus and the most important effect in relation to the disclosure).

Throughout the disclosure, the use of the terms "first", "second", "third", "fourth", "primary", "secondary", "tertiary" etc. does not imply any particular order or importance but are included merely to identify individual elements. Furthermore, the labelling of a first element does not imply the presence of a second element and vice versa.

Disclosed is a sensor patch for attachment to a base plate for an ostomy appliance. Such as to facilitate detection of moisture propagation in the adhesive material provided for attaching the base plate to the skin surface of a user as well as detection of increased risk of leakage. For example, the sensor patch may allow electronic measurements of performance of the base plate and/or to facilitate detection of increasing risks of leakage and/or to facilitate detection of decreasing adherence of the base plate to the skin of the user.

The ostomy appliance comprises a base plate and an ostomy pouch (also referred to as an ostomy bag). The ostomy appliance may be a colostomy appliance, an ileostomy appliance or a urostomy appliance. The ostomy appliance may be a two-part ostomy appliance, i.e. the base plate and the ostomy pouch may be releasably coupled e.g. with a mechanical and/or an adhesive coupling, e.g. to allow that a plurality of ostomy pouches can be utilized (exchanged) with one base plate. For example, the base plate may comprise a coupling ring for coupling an ostomy pouch to the base plate. Further, a two-part ostomy appliance may facilitate correct application of the base plate to skin, e.g. to an improved user sight of the stomal region. Alternatively, the ostomy appliance may be a one-part ostomy appliance, i.e. the base plate and the ostomy pouch may be fixedly attached to each other. The base plate is configured for coupling to a user's stoma and/or skin surrounding the stoma, such as a peristomal skin area.

The base plate may comprise a first adhesive layer, i.e. a first layer of an adhesive material. During use, a proximal surface of the first adhesive layer adheres to the user's skin in the peristomal area and/or to additional seals, such as sealing paste, sealing tape and/or sealing ring. The first adhesive layer may be made of a first composition. The first composition may comprise one or more polyisobutenes and/or styrene-isoprene-styrene. The first composition may comprise one or more hydrocolloids. The first composition may comprise one or more water soluble or water swellable hydrocolloids. The first composition may be a pressure sensitive adhesive composition suitable for medical purposes comprising a rubbery elastomeric base and one or more water soluble or water swellable hydrocolloids. The first adhesive layer may comprise a distal surface and a proximal surface. The proximal surface of the first adhesive layer may be configured to adhere to the user's skin. The distal surface of the first adhesive layer may be configured to face away from the skin of the user.

The first adhesive layer may form the adhesive surface of the base plate adapted for attachment of the base plate to the skin surface of the user. The first adhesive layer may form part of the adhesive surface of the base plate adapted for attachment of the base plate to the skin surface of the user.

The base plate may comprise a second adhesive layer, i.e. a second layer of an adhesive material, also denoted rim adhesive layer. The second adhesive layer may be of a different adhesive material than the first adhesive layer. The second adhesive layer may be made of a second composition. The second composition may comprise one or more polyisobutenes and/or styrene-isoprene-styrene. The second composition may comprise one or more hydrocolloids. The second composition may comprise one or more water soluble or water swellable hydrocolloids. The second composition may be a pressure sensitive adhesive composition suitable for medical purposes comprising a rubbery elastomeric base and one or more water soluble or water swellable hydrocolloids. The second adhesive layer may comprise a distal surface and a proximal surface.

The proximal surface of the second adhesive layer may be configured to adhere to the user's skin, e.g. at least at a rim portion of the second adhesive layer. The distal surface of the second adhesive layer may be configured to face away from the skin of the user. The second adhesive layer may be covering a larger area than the first adhesive layer, e.g. such that the proximal surface of the second adhesive layer forms an adhesive rim surrounding the first adhesive layer.

Different ratio of contents may change properties of the first adhesive layer and/or the second adhesive layer. The second adhesive layer and the first adhesive layer may have different properties. The second adhesive layer (second composition) and the first adhesive layer (first composition) may have different ratios of polyisobutenes, styrene-isoprene-styrene, and/or hydrocolloids. For example, the second adhesive layer may provide a stronger attachment to the skin compared to attachment to the skin provided by the first adhesive layer. Alternatively or additionally, the second adhesive layer may be thinner than the first adhesive layer. Alternatively or additionally, the second adhesive layer may be less water and/or sweat absorbing than the first adhesive layer. Alternatively or additionally, the second adhesive layer may be less mouldable than the first adhesive layer. The second adhesive layer may provide a second barrier against leakage.

The second adhesive layer may form part of the adhesive surface of the base plate adapted for attachment of the base plate to the skin surface of the user. The first adhesive layer and the second adhesive layer may form the adhesive surface of the base plate adapted for attachment of the base plate to the skin surface of the user.

The first adhesive layer and/or the second adhesive layer may comprise a centre portion with a centre thickness, and an outer rim portion surrounding the centre portion. The outer rim portion may have an outer rim thickness, e.g. decreasing along a radial direction from adjacent the centre portion to an outer periphery of the first adhesive layer and/or the second adhesive layer. The outer rim thickness may be decreasing convexly, concavely, or substantially linearly along the radial direction from adjacent the centre portion to the outer periphery. The outer rim thickness adjacent the centre portion may be the centre thickness. The outer rim thickness at the outer periphery may be a minimum outer rim thickness. The centre thickness may be between 0.5 mm and 1.5 mm. The minimum outer rim thickness may be less than 0.5 mm, such as less than 0.4 mm, such as less than 0.3 mm, such as less than 0.1 mm.

The first adhesive layer and/or the second adhesive layer may surround an opening, such as the stomal opening. The first adhesive layer and/or the second adhesive layer may have an inner rim portion being surrounded by the centre portion. The inner rim portion may have an inner rim thickness increasing along a radial direction from an inner periphery of the first adhesive layer and/or the second adhesive layer to the centre portion. The inner rim thickness may be increasing convexly, concavely, or substantially linearly along the radial direction from the inner periphery to the centre portion. The inner rim thickness adjacent the centre portion may be the centre thickness. The inner rim thickness at the inner periphery may be a minimum inner rim thickness. The minimum inner rim thickness may be less than 0.5 mm, such as less than 0.4 mm, such as less than 0.3 mm, such as less than 0.1 mm.

Providing a base plate wherein the adhesive, such as the first adhesive layer and/or the second adhesive layer, has a decreasing outer rim and/or an increasing inner rim facilitates a smoother transition between the base plate and the skin of the user at the edge of the base plate. Thereby, the risk of clothes adhering to the edge of the base plate and potentially peeling the base plate off the skin, may be reduced. Thus, decreasing the risk of leakage caused by the base plate adhering insufficiently to the skin of the user.

The base plate may comprise a release liner, which may be peeled off by the user prior to applying the base plate to the skin. The release liner may be configured to protect the adhesive layers prior to applying the base plate to the skin. The release liner may comprise a distal surface and a proximal surface. The release liner may be configured to, e.g. prior to applying the base plate to the skin, covering the proximal surface of the first adhesive layer and/or covering the proximal surface of the second adhesive layer, such as the proximal surface of the second adhesive layer not covered by the first adhesive layer. The distal surface of the release liner may be configured to, e.g. prior to applying the base plate to the skin, face the proximal surface of the first adhesive layer and/or the proximal surface of the second adhesive layer, such as the proximal surface of the second adhesive layer not covered by the first adhesive layer.

The base plate may comprise a backing layer. The backing layer may be a protective layer protecting the adhesive layers, such as the first adhesive layer and/or the second adhesive layer from external strains and stress during use. Furthermore, the backing layer may also cover the adhesive layers, such as the first adhesive layer and/or the second adhesive layer, such that the adhesive layers do not adhere to clothes worn on top of the base plate. The backing layer may comprise a distal surface and a proximal surface. The distal surface of the backing layer may be configured to face away from the skin of the user. The proximal surface of the backing layer may be facing the second adhesive layer. The second adhesive layer may be provided on the proximal surface of the backing layer.

The base plate may comprise a stomal opening. Each layer of the base plate may comprise stomal openings for collectively forming the stomal opening of the base plate. The stomal opening may be provided in a centre portion of the base plate. The centre portion of the base plate may be surrounding the stomal opening. The stomal opening may be configured to receive a stoma of the user and/or the stomal opening may be configured to allow output from the stoma to pass through the stomal opening an into an ostomy pouch attached to the base plate. For example, the stomal opening may be configured to allow passage of output from the proximal side of the base plate to a distal side of the base plate. The size and/or shape of the stomal opening may typically be adjusted by the user or nurse before application of the base plate to accommodate the user's stoma.

The sensor patch according to the present disclosure is adapted for attachment to the base plate. For example, the sensor patch may be configured to be positioned between the skin of the user and the proximal side of the base plate. For example, the sensor patch may be adapted for attachment to the first adhesive layer of the base plate. For example, a distal side of the sensor patch may be configured to be facing the proximal surface of the first adhesive layer of the base plate. For example, the sensor patch, such as a distal side of the sensor patch may be configured to adhere to the proximal surface of the first adhesive layer of the base plate.

The sensor patch may comprise a stomal opening and/or the sensor patch may be adapted to form a stomal opening. Each layer of the sensor patch, as described below, may comprise stomal openings and/or be adapted to form a stomal opening for collectively forming the stomal opening of the sensor patch. The stomal opening of the sensor patch may be configured to be aligned with the stomal opening of the base plate, such as to collectively form the stomal opening of the combined base plate and sensor patch. The size and/or shape of the stomal opening of the sensor patch may be adjusted by the user or nurse before application of the sensor patch to accommodate the user's stoma. The size and/or shape of the stomal opening of the sensor patch may be adjusted together with adjustment of the stomal opening of the base plate, e.g. after the sensor patch has been attached to the base plate. The stomal opening(s) may have a centre point.

The sensor patch comprises a sensor assembly. The sensor assembly may form a sensor assembly layer. The sensor assembly may have a distal side and a proximal side. The sensor patch may be configured to be positioned on the base plate such that the distal surface of the sensor assembly is coupled to the proximal adhesive surface of the base plate.

The sensor assembly comprises a plurality of electrodes. The plurality of electrodes includes a first electrode and a second electrode for forming a first sensor. The plurality of electrodes may include a third electrode, a fourth electrode, a fifth electrode and/or a sixth electrode. The first electrode may be a common ground electrode. For example, a second sensor may be formed by the first electrode and the third electrode, a third sensor may be formed by the first electrode and the fourth electrode, a fourth electrode may be formed by the first electrode and the fifth electrode, and/or a fifth electrode may be formed by the first electrode and the sixth electrode. Each electrode may have respective connection parts for connecting the electrodes to respective terminal elements of a monitor device.

The plurality of electrodes is electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

The plurality of electrodes may form loops and/or open loops. Open loop electrode(s) enables electrode arrangement in few or a single electrode layer.

The sensor assembly may comprise a support layer, e.g. with a proximal surface and a distal surface. The plurality of electrodes may be provided, such as formed, on the proximal surface of the support layer, e.g. the plurality of electrodes may be positioned on the proximal surface of the support layer.

The sensor assembly may comprise a masking element, e.g. with a proximal surface and a distal surface. The masking element may be configured to electrically insulate at least parts of the plurality of electrodes from proximal layers, such as a first adhesive sensor layer. The masking element may cover or overlap parts of the plurality electrodes, e.g. when seen in the axial direction.

The sensor patch comprises a first adhesive sensor layer, e.g. with a proximal side and a distal side. The first adhesive sensor layer may be arranged on a proximal side of the sensor assembly. The first adhesive sensor layer, such as the proximal side of the first adhesive sensor layer, forms the proximal side of the sensor patch. The proximal side of the first adhesive sensor layer may be configured to adhere to the user's skin. Thus, after being applied to the base plate, the combined base plate and sensor patch may form an adhesive proximal surface configured to be applied to the skin surface of the user. The first adhesive sensor layer may be made of a first adhesive sensor material, such as the first composition, the second composition or a third composition. The third composition may comprise one or more polyisobutenes and/or styrene-isoprene-styrene. The third composition may comprise one or more hydrocolloids. The third composition may comprise one or more water soluble or water swellable hydrocolloids. The third composition may be a pressure sensitive adhesive composition suitable for medical purposes comprising a rubbery elastomeric base and one or more water soluble or water swellable hydrocolloids.

The first adhesive sensor layer comprises a first centre portion. The first centre portion has a first centre thickness. The first adhesive sensor layer comprises a first outer rim portion surrounding the first centre portion. The first outer rim portion has a first outer rim thickness decreasing along a radial direction from adjacent the first centre portion to a first outer periphery of the first adhesive sensor layer. The first outer rim thickness may be decreasing convexly, concavely, or substantially linearly along the radial direction from adjacent the first centre portion to the first outer periphery of the first adhesive sensor layer. The first outer rim thickness adjacent the first centre portion is the first centre thickness. The first outer rim thickness at the first outer periphery of the first adhesive sensor layer is a first minimum outer rim thickness. The first centre thickness may be between 0.5 mm and 1.5 mm. The first minimum outer rim thickness may be less than 0.5 mm, such as less than 0.4 mm, such as less than 0.3 mm, such as less than 0.1 mm. A radial distance from the centre point to the first outer rim portion adjacent the first centre portion may be between 15-35 mm. A radial distance from the first outer rim portion adjacent the first centre portion to the first outer periphery of the first adhesive sensor layer may be between 0.5-20 mm. A radial distance from the centre point to the first outer periphery of the first adhesive sensor layer may be between 15.5-55 mm, such as between 20-45 mm, such as between 25-40 mm, such as between 30-35 mm.

Thereby is provided that the sensor patch, in particular the first adhesive sensor layer of the sensor patch, has a chamfered edge, whereby a smooth transition between an adhesive surface of a base plate and the sensor patch attached thereto is provided. The smooth transition reduces the potentially unfavourable effects of having a sensor patch attached to the adhesive surface of the base plate. For example, the presence of an unchamfered edge may cause increased risk of leakage from the base plate, e.g. due to insufficient adhesion to the skin surface, or cause increased risk of skin irritation, e.g. due to an unchamfered edge irritating the skin.

The first adhesive sensor layer may surround an opening, such as the stomal opening and/or an opening larger than the stomal opening. The first adhesive sensor layer may have a first inner rim portion being surrounded by the first centre portion. The first inner rim portion may have a first inner rim thickness increasing along a radial direction from a first inner periphery of the first adhesive sensor layer to the first centre portion. The first inner rim thickness may be increasing convexly, concavely, or substantially linearly along the radial direction from the first inner periphery of the first adhesive sensor layer to the first centre portion. The first inner rim thickness adjacent the first centre portion may be the first centre thickness. The first inner rim thickness at the first inner periphery of the first adhesive sensor layer may be a first minimum inner rim thickness. The first minimum inner rim thickness may be less than 0.5 mm, such as less than 0.4 mm, such as less than 0.3 mm, such as less than 0.1 mm. A radial distance from the centre point to the first inner rim portion adjacent the first centre portion may be between 10-30 mm. A radial distance from the first inner periphery of the first adhesive sensor layer to the first centre portion, such as the first centre portion adjacent the first inner rim portion, may be between 0.5-20 mm. A radial distance from the centre point to the first centre portion, such as the first centre portion adjacent the inner rim portion, may be between 10.5-50 mm, such as between 15-40 mm, such as between 20-35 mm, such as between 20-30 mm.

In manufacturing of the sensor patch, the first adhesive sensor material may be provided and a layer of the first adhesive sensor material for forming the first adhesive sensor layer may be laid out to form the first centre portion, the first outer rim portion and/or the first inner rim portion according to the above.

The first adhesive sensor layer may comprise hydrocolloids. The hydrocolloids being arranged along the first outer periphery of the first adhesive sensor layer, such as the hydrocolloids being arranged in the first outer rim portion, may have a first outer rim average grain size and/or a first outer rim maximum grain size. The hydrocolloids being arranged in the first centre portion may have a first centre average gran size and/or a first centre maximum grain size. The hydrocolloids being arranged along the first inner periphery of the first adhesive sensor layer, such as the hydrocolloids being arranged in the first inner rim portion, may have a first inner rim average grain size and/or a first inner rim maximum grain size. The hydrocolloids may have an average grain size of less than 0.2 mm, such as less than 0.1 mm. The hydrocolloids may have a maximum grain size of less than 0.3 mm, such as less than 0.2 mm, such as less than 0.1 mm. The first outer rim average grain size may be less than 0.2 mm, such as less than 0.1 mm. The first outer rim maximum grain size may be less than 0.3 mm, such as less than 0.2 mm, such as less than 0.1 mm. The first inner rim average grain size may be less than 0.2 mm, such as less than 0.1 mm. The first inner rim maximum grain size may be less than 0.3 mm, such as less than 0.2 mm, such as less than 0.1 mm. The first centre average grain size may be less than 0.2 mm, such as less than 0.1 mm. The first centre maximum grain size may be less than 0.3 mm, such as less than 0.2 mm, such as less than 0.1 mm.

The hydrocolloids may be arranged such that the first outer rim average/maximum grain size and/or the first inner rim average/maximum grain size is less than the centre average/maximum grain size. For example, the first outer rim average/maximum grain size and/or the first inner rim average/maximum grain size may be less than half of the centre average/maximum grain size. Alternatively, the first outer rim average/maximum grain size, the first inner rim average/maximum grain size and the centre average/maximum grain size may be substantially the same.

The hydrocolloids may be sorted in order to achieve a smaller grain size, e.g. to allow for a thinner outer and/or inner periphery of the first adhesive sensor layer. Providing the first adhesive sensor material for forming the first adhesive sensor layer, may comprise sorting hydrocolloids of the first adhesive sensor material according to grain size. For example, sorting the hydrocolloids of the first adhesive sensor material may comprise sorting the hydrocolloids to achieve an average/maximum grain size of the hydrocolloids of less than 0.3 mm, such as less than 0.2 mm, such as less than 0.1 mm. Thereby, the properties of hydrocolloids are retained despite reducing the thickness of the adhesive comprising the hydrocolloids. Alternatively or additionally, laying out the layer of the first adhesive sensor material may comprise laying out the layer of the first adhesive sensor material for forming the first centre portion with hydrocolloids having the first centre average/maximum grain size, laying out the layer of the first adhesive sensor material for forming the first outer rim portion with hydrocolloids having the first outer rim average/maximum grain size, and/or laying out the layer of the first adhesive sensor material for forming the first inner rim portion with hydrocolloids having the first inner rim average/maximum grain size.

Laying out the layer of the first adhesive sensor material for forming the first adhesive sensor layer may comprise extruding the first adhesive sensor layer. Alternatively or additionally, laying out the layer of the first adhesive sensor material for forming the first adhesive sensor layer may comprises moulding, such as injection moulding, of the first adhesive sensor layer. The mould may have a non-planar surface shaped to provide the shapes of the first outer rim, the first centre portion, and/or the first inner rim according to the above. Alternatively or additionally, laying out the layer of the first adhesive sensor material for forming the first adhesive sensor layer may comprise scraping the first adhesive sensor material onto a non-planar surface, e.g. a distal surface of a first release liner or a proximal surface of the sensor assembly, shaped to provide the profile of the first outer rim, the first centre portion, and/or the first inner rim according to the above.

In embodiments, the sensor patch comprises a second adhesive sensor layer, e.g. with a proximal side and a distal side. The second adhesive sensor layer may be arranged on a distal side of the sensor assembly. The distal side of the second adhesive sensor layer may be configured to adhere to the proximal surface of the base plate, such as the proximal surface of the first adhesive layer of the base plate. The second adhesive sensor layer may be made of a second adhesive sensor material, such as the first composition, the second composition, the third composition, or a fourth composition. The fourth composition may comprise one or more polyisobutenes and/or styrene-isoprene-styrene. The fourth composition may comprise one or more hydrocolloids. The fourth composition may comprise one or more water soluble or water swellable hydrocolloids. The fourth composition may be a pressure sensitive adhesive composition suitable for medical purposes comprising a rubbery elastomeric base and one or more water soluble or water swellable hydrocolloids. The second adhesive sensor material may be the same as the first adhesive sensor material. The second adhesive sensor layer, when arranged on the distal side of the sensor assembly, may provide a symmetrical sensor patch, such that each side of the sensor patch may be adhered to the skin surface, or the second adhesive sensor layer may serve to encapsulate the sensor assembly.

The second adhesive sensor layer may comprise a second centre portion. The second centre portion may have a second centre thickness. The second adhesive sensor layer may comprise a second outer rim portion surrounding the second centre portion. The second outer rim portion may have a second outer rim thickness, e.g. decreasing along a radial direction from adjacent the second centre portion to a second outer periphery of the second adhesive sensor layer. The second outer rim thickness may be decreasing convexly, concavely, or substantially linearly along the radial direction from adjacent the second centre portion to the second outer periphery of the second adhesive sensor layer. The second outer rim thickness adjacent the second centre portion may be the second centre thickness. The second outer rim thickness at the second outer periphery of the second adhesive sensor layer may be a second minimum outer rim thickness. The second centre thickness may be between 0.5 mm and 1.5 mm. The second minimum outer rim thickness may be less than 0.5 mm, such as less than 0.4 mm, such as less than 0.3 mm, such as less than 0.1 mm. A radial distance from the centre point to the second outer rim portion adjacent the second centre portion may be between 15-35 mm. A radial distance from the second outer rim portion adjacent the second centre portion to the second outer periphery of the second adhesive sensor layer may be between 0.5-25 mm. A radial distance from the second centre point to the second outer periphery of the second adhesive sensor layer may be between 15.5-60 mm, such as between 20-50 mm, such as between 25-40 mm, such as between 30-35 mm.

The second adhesive sensor layer may surround an opening, such as the stomal opening and/or an opening larger than the stomal opening. The second adhesive sensor layer may have a second inner rim portion being surrounded by the second centre portion. The second inner rim portion may have a second inner rim thickness increasing along a radial direction from a second inner periphery of the second adhesive sensor layer to the second centre portion. The second inner rim thickness may be increasing convexly, concavely, or substantially linearly along the radial direction from the second inner periphery of the second adhesive sensor layer to the second centre portion. The second inner rim thickness adjacent the second centre portion may be the second centre thickness. The second inner rim thickness at the second inner periphery of the second adhesive sensor layer may be a second minimum inner rim thickness. The second minimum inner rim thickness may be less than 0.5 mm, such as less than 0.4 mm, such as less than 0.3 mm, such as less than 0.1 mm. A radial distance from the centre point to the second inner rim portion adjacent the second centre portion may be between 10-30 mm. A radial distance from the second inner periphery of the second adhesive sensor layer to the second centre portion, such as the second centre portion adjacent the second inner rim portion, may be between 0.5-20 mm. A radial distance from the centre point to the second centre portion, such as the second centre portion adjacent the second inner rim portion, may be between 10.5-50 mm, such as between 15-40 mm, such as between 20-35 mm, such as between 20-30 mm.

In manufacturing of the sensor patch, the second adhesive sensor material may be provided and a layer of the second adhesive sensor material for forming the second adhesive sensor layer may be laid out to form the second centre portion, the second outer rim portion and/or the second inner rim portion according to the above.

The second adhesive sensor layer may comprise hydrocolloids. The hydrocolloids being arranged along the second outer periphery of the second adhesive sensor layer, such as the hydrocolloids being arranged in the second outer rim portion, may have a second outer rim average grain size and/or a second outer rim maximum grain size. The hydrocolloids being arranged in the second centre portion may have a second centre average gran size and/or a second centre maximum grain size. The hydrocolloids being arranged along the second inner periphery of the second adhesive sensor layer, such as the hydrocolloids being arranged in the second inner rim portion, may have a second inner rim average grain size and/or a second inner rim maximum grain size. The hydrocolloids may have an average grain size of less than 0.2 mm, such as less than 0.1 mm. The hydrocolloids may have a maximum grain size of less than 0.3 mm, such as less than 0.2 mm, such as less than 0.1 mm. The second outer rim average grain size may be less than 0.2 mm, such as less than 0.1 mm. The second outer rim maximum grain size may be less than 0.3 mm, such as less than 0.2 mm, such as less than 0.1 mm. The second inner rim average grain size may be less than 0.2 mm, such as less than 0.1 mm. The second inner rim maximum grain size may be less than 0.3 mm, such as less than 0.2 mm, such as less than 0.1 mm. The second centre average grain size may be less than 0.2 mm, such as less than 0.1 mm. The second centre maximum grain size may be less than 0.3 mm, such as less than 0.2 mm, such as less than 0.1 mm.

The hydrocolloids may be arranged such that the second outer rim average/maximum grain size and/or the second inner rim average/maximum grain size is less than the centre average/maximum grain size. For example, the second outer rim average/maximum grain size and/or the second inner rim average/maximum grain size may be less than half of the centre average/maximum grain size. Alternatively, the second outer rim average/maximum grain size, the second inner rim average/maximum grain size and the centre average/maximum grain size may be substantially the same.

Providing the second adhesive sensor material for forming the second adhesive sensor layer, may comprise sorting hydrocolloids of the second adhesive sensor material according to grain size. For example, sorting the hydrocolloids of the second adhesive sensor material may comprise sorting the hydrocolloids to achieve an average/maximum grain size of the hydrocolloids of less than 0.3 mm, such as less than 0.2 mm, such as less than 0.1 mm. Alternatively or additionally, laying out the layer of the second adhesive sensor material may comprise laying out the layer of the second adhesive sensor material for forming the second centre portion with hydrocolloids having the second centre average/maximum grain size, laying out the layer of the second adhesive sensor material for forming the second outer rim portion with hydrocolloids having the second outer rim average/maximum grain size, and/or laying out the layer of the second adhesive sensor material for forming the second inner rim portion with hydrocolloids having the second inner rim average/maximum grain size.

Laying out the layer of the second adhesive sensor material for forming the second adhesive sensor layer may comprise extruding the second adhesive sensor layer. Alternatively or additionally, laying out the layer of the second adhesive sensor material for forming the second adhesive sensor layer may comprises moulding, such as injection moulding, of the second adhesive sensor layer. The mould may have a non-planar surface shaped to provide the shapes of the second outer rim, the second centre portion, and/or the second inner rim according to the above. Alternatively or additionally, laying out the layer of the second adhesive sensor material for forming the second adhesive sensor layer may comprise scraping the second adhesive sensor material onto a non-planar surface, e.g. a proximal surface of a second release liner or a distal surface of the sensor assembly, shaped to provide the profile of the second outer rim, the second centre portion, and/or the second inner rim according to the above.

The sensor assembly comprising the plurality of electrodes may be arranged on the distal side of the first adhesive sensor layer and/or on the proximal side of the second adhesive sensor layer. The plurality of electrodes of the sensor assembly may be arranged in relation to the inner and/or outer rim portions of the first adhesive sensor layer and/or second adhesive sensor layer. In particular, the plurality of electrodes may be arranged such as to measure over parts of the adhesive layers where the adhesive layers have a substantially uniform thickness. Such arrangement may facilitate reliability of the measurements and/or the subsequent interpretation of the measured values. The plurality of electrodes of the sensor assembly may form loops, such as open loops or closed loops, e.g. surrounding the centre point. The first electrode may form a first loop, the second electrode may form a second loop, the third electrode may form a third loop, the fourth electrode may form a fourth loop, the fifth electrode may form a fifth loop, and/or the sixth electrode may form a sixth loop. An electrode, such as the first electrode, may form a plurality of loops, e.g. the first electrode may form a plurality of first loops, e.g. including a first primary loop, a first secondary loop, a first tertiary loop, etc.

A radial distance from the centre point to the first loop formed by the first electrode, to the second loop formed by the second electrode, to the third loop formed by the third electrode, to the fourth loop formed by the fourth electrode, to the fifth loop formed by the fifth electrode, and/or to the sixth loop formed by the sixth electrode, may be less than the radial distance from the centre point to the first outer rim portion, such as to the first outer rim portion adjacent the first centre portion. A radial distance from the centre point to the first loop formed by the first electrode, to the second loop formed by the second electrode, to the third loop formed by the third electrode, to the fourth loop formed by the fourth electrode, to the fifth loop formed by the fifth electrode, and/or to the sixth loop formed by the sixth electrode, may be more than the radial distance from the centre point to the first inner rim portion, such as to the first inner rim portion adjacent the first centre portion.

A radial distance from the centre point to the first loop formed by the first electrode, to the second loop formed by the second electrode, to the third loop formed by the third electrode, to the fourth loop formed by the fourth electrode, to the fifth loop formed by the fifth electrode, and/or to the sixth loop formed by the sixth electrode, may be less than the radial distance from the centre point to the second outer rim portion, such as to the second outer rim portion adjacent the second centre portion. A radial distance from the centre point to the first loop formed by the first electrode, to the second loop formed by the second electrode, to the third loop formed by the third electrode, to the fourth loop formed by the fourth electrode, to the fifth loop formed by the fifth electrode, and/or to the sixth loop formed by the sixth electrode, may be more than the radial distance from the centre point to the second inner rim portion, such as to the second inner rim portion adjacent the second centre portion.

A radial distance from the centre point to the second loop may be less than the radial distance from the centre point to the first loop. A radial distance from the centre point to the third loop may be less than the radial distance from the centre point to the second loop. A radial distance from the centre point to the fourth loop may be less than the radial distance from the centre point to the third loop. A radial distance from the centre point to the fifth loop may be less than the radial distance from the centre point to the fourth loop. A radial distance from the centre point to the sixth loop may be less than the radial distance from the centre point to the fifth loop.

The sensor patch may comprise one or more sensor release liner(s), such as a first sensor release liner and/or a second sensor release liner.

The first sensor release liner may comprise a distal surface and a proximal surface. The first sensor release liner may be arranged to protect the first adhesive sensor layer, e.g. the distal surface of the first sensor release liner may face the proximal surface of the first adhesive sensor layer. The first sensor release liner may be configured to be peeled off by the user prior to application of the base plate with the attached sensor patch to the skin. The layer of the first adhesive sensor material may be laid out on the distal side of the first sensor release liner.

The second sensor release liner may comprise a distal surface and a proximal surface. The second sensor release liner may be arranged to protect the second adhesive sensor layer, e.g. the proximal surface of the second sensor release liner may face the distal surface of the second adhesive sensor layer. The second sensor release liner may be configured to be peeled off by the user prior to attaching the sensor patch to the base plate. The layer of the second adhesive sensor material may be laid out on the proximal side of the second sensor release liner.

The sensor patch may comprise a monitor interface. The monitor interface may be configured for electrically and/or mechanically connecting the sensor patch, such as the plurality of electrodes of the sensor patch, to the monitor device. The monitor interface may be configured for wirelessly connecting the sensor patch, such as the electrodes of the sensor patch, to the monitor device. The monitor interface may be configured to electrically and/or mechanically couple the sensor patch and the monitor device.

The disclosed sensor patch could be combined with the base plate, such as to form a monolithic, one-piece base plate, e.g. integrated with a sensor assembly part, such as the sensor assembly part as described above. For example, the base plate may comprise a sensor assembly, such as the sensor assembly as described with respect to the sensor patch. For example, the sensor assembly may be positioned between the first adhesive layer and the second adhesive layer. The distal surface of the first adhesive layer may be facing the proximal side of the sensor assembly and/or the distal side of the sensor assembly may be facing the proximal side of the second adhesive layer. For example, the first adhesive layer and/or the second adhesive layer of the base plate may be provided as described with respect to the first adhesive sensor layer and/or the second adhesive sensor layer, respectively.

The radial distance from the centre point to the first loop formed by the first electrode, to the second loop formed by the second electrode, to the third loop formed by the third electrode, to the fourth loop formed by the fourth electrode, to the fifth loop formed by the fifth electrode, and/or to the sixth loop formed by the sixth electrode, may be less than the radial distance from the centre point to the outer rim portion of the first adhesive layer and/or the second adhesive layer, such as to the outer rim portion adjacent the centre portion of the first adhesive layer and/or the second adhesive layer. The radial distance from the centre point to the first loop formed by the first electrode, to the second loop formed by the second electrode, to the third loop formed by the third electrode, to the fourth loop formed by the fourth electrode, to the fifth loop formed by the fifth electrode, and/or to the sixth loop formed by the sixth electrode, may be more than the radial distance from the centre point to the inner rim portion of the first adhesive layer and/or the second adhesive layer, such as to the inner rim portion adjacent the centre portion of the first adhesive layer and/or the second adhesive layer.

FIG. 1 schematically illustrates an exploded view of an exemplary base plate 4 of an ostomy appliance. The base plate 4 comprises a first adhesive layer 200 having a distal surface 200A and a proximal surface 200B. During use, the proximal surface 200B of the first adhesive layer 200 adheres to the user's skin. The base plate 4 comprises a second adhesive layer 202 having a distal surface 202A and a proximal surface 202B. As illustrated, the second adhesive layer 202 spans a larger surface area than the first adhesive layer 200, such as to provide a rim of the proximal surface 202 of the second adhesive layer 202 surrounding the proximal surface 200 of the first adhesive layer 200.

The base plate 4 comprises a release liner 206, which may be peeled off by the user prior to applying the base plate 4 to the skin. The release liner 206 comprises a distal surface 206A and a proximal surface 206B. The distal surface 206A of the release liner 206 is covering the proximal surface of the first adhesive layer 200 and covering the proximal surface of the second adhesive layer 202 not covered by the first adhesive layer 200.

The base plate 4 comprises a backing layer 208. The backing layer 208 is a protective layer protecting the adhesive layers, such as the first adhesive layer 200 and/or the second adhesive layer 202 from external strains and stress during use. Furthermore, the backing layer 208 also covers the adhesive layers, such as the first adhesive layer 200 and/or the second adhesive layer 202, such that the adhesive layers 200, 202 does not adhere to clothes worn on top of the base plate 4. The backing layer 208 comprises a distal surface 208A and a proximal surface 208B. The distal surface 208A of the backing layer 208 is configured to face away from the skin of the user. The proximal surface 208B of the backing layer 208 is covering the second adhesive layer 202.

The base plate 4 is a two-part ostomy appliance, thus comprising a coupling ring 209 for coupling an ostomy pouch to the base plate 4, such as to a distal side of the base plate 4.

The base plate 4 comprises a stomal opening. The layers of the base plate 4, such as the first adhesive layer 200, the second adhesive layer 202 and the backing layer 208 as illustrated, may comprise stomal openings 18 for collectively forming the stomal opening of the base plate.

Figure 2:
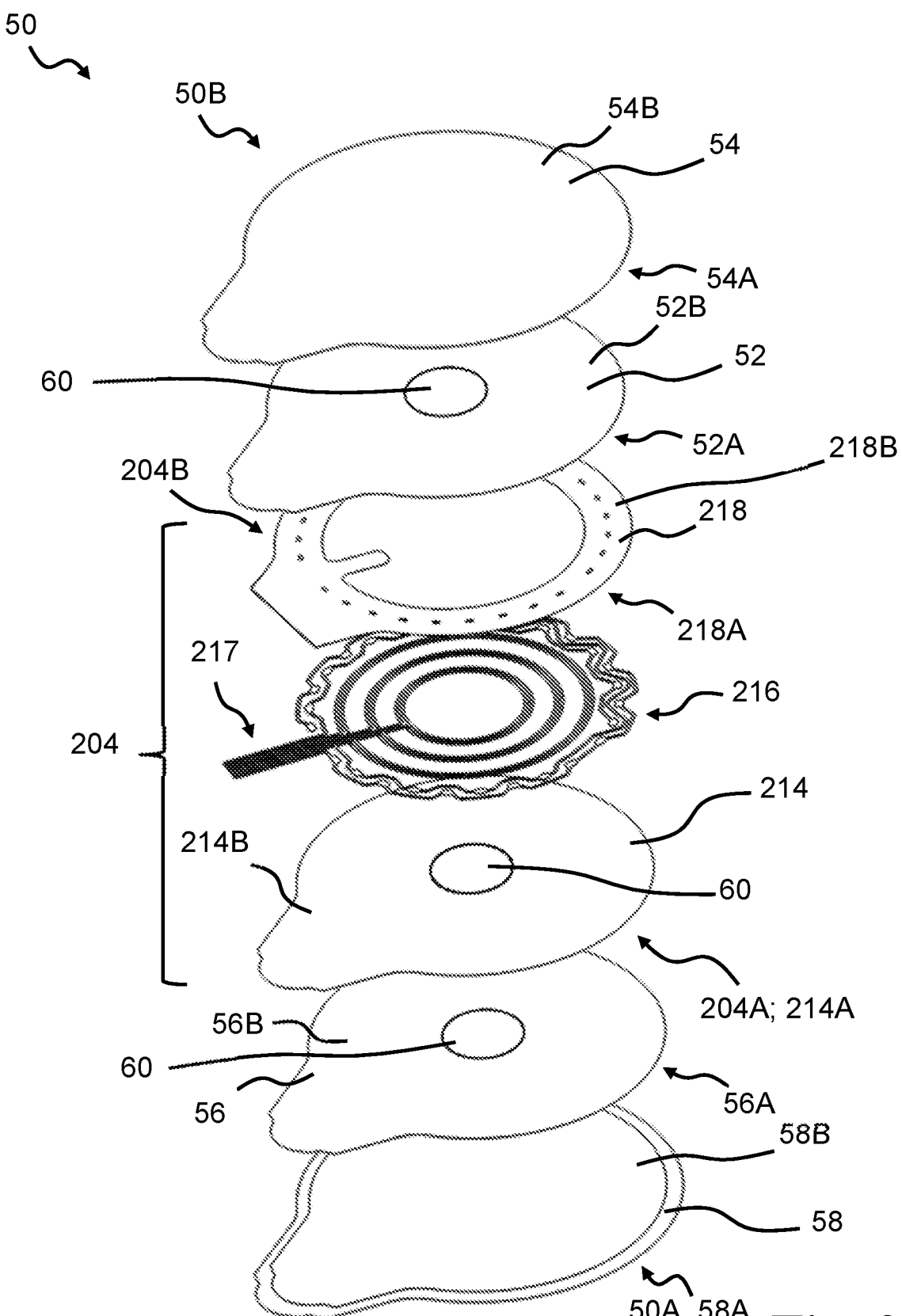

FIG. 2 schematically illustrates an exploded view of an exemplary sensor patch 50, such as a sensor patch 50 being adapted for attachment to a base plate, such as the base plate 4 as illustrated in FIG. 1. The sensor patch 50 is configured to be positioned between the skin of the user and the proximal side of the base plate 4. For example, the sensor patch may be adapted for attachment to the first adhesive layer 200, such as the proximal surface 200B of the first adhesive layer 200, of the base plate 4. The sensor patch 50 is configured to be attached to the base plate such that the distal side 50A of the sensor patch 50 is attached to the proximal side of the base plate, such as to the proximal surface 200B of the first adhesive layer 200 of the base plate 4.

The sensor patch 50 comprises a sensor assembly 204 comprising a plurality of electrodes 216. Each electrode 216 has respective connection parts 217 for connecting the plurality of electrodes 216 to respective terminal elements of a monitor device. The sensor assembly 204 may form a sensor assembly layer.

The sensor assembly 204 has a distal side 204A and a proximal side 204B. The sensor assembly 204 comprises a support layer 214 with a proximal surface 214B. The electrodes 216 may be provided, such as formed, on the proximal surface 214B of the support layer 214, e.g. the electrodes 216 may be positioned on the proximal surface 214B of the support layer 214.

The electrode assembly 204 comprises a masking element 218 having a distal surface 218A and a proximal surface 218B. The masking element 218 is configured to electrically insulate at least parts of electrodes 216 from adjacent layers, such as the first adhesive sensor layer 52. The masking element 218 covers or overlap with parts of the electrodes 216 when seen in the axial direction.

The sensor patch 50 comprises a first adhesive sensor layer 52, with a proximal side 52B and a distal side 52A. The first adhesive sensor layer 52 is arranged on the proximal side 204B of the sensor assembly 204. The proximal side 52B of the first adhesive sensor layer 52 is configured to adhere to the user's skin. Thus, after being applied to the base plate, the combined base plate and sensor patch 50 forms an adhesive proximal surface configured to be applied to the skin surface of the user.

The sensor patch comprises a first sensor release liner 54. The first sensor release liner 54 may comprise a distal surface 54A and a proximal surface 54B. The first sensor release liner 54 may be arranged to protect the first adhesive sensor layer 52. The distal surface 54A of the first sensor release liner 54 is facing the proximal surface 52B of the first adhesive sensor layer 52. The first sensor release liner 54 is configured to be peeled off by the user prior to application of the base plate with the attached sensor patch to the skin. The first adhesive sensor layer 52 may be laid out on the distal side 54A of the first sensor release liner 54.

The sensor patch 50 comprises a second adhesive sensor layer 56, with a proximal side 56B and a distal side 56A. The second adhesive sensor layer 56 is arranged on the distal side 204A of the sensor assembly 204. The proximal side 56B of the second adhesive sensor layer 52 is configured to adhere to the base plate, such as the proximal surface of the first adhesive layer of the base plate.

The exemplary sensor patch comprises a second sensor release liner 58. The second sensor release liner 58 may comprise a distal surface 58A and a proximal surface 58B. The second sensor release liner 58 may be arranged to protect the second adhesive sensor layer 56. The proximal surface 58B of the second sensor release liner 58 is facing the distal surface 56A of the second adhesive sensor layer 56. The second sensor release liner 58 is configured to be peeled off by the user prior to application of the sensor patch to the base plate. The second adhesive sensor layer 56 may be laid out on the proximal side 58B of the second sensor release liner 58.

Whereas the illustrated exemplary sensor patch 50 comprises a second adhesive sensor layer 56 arranged on the distal side 204A of the sensor assembly 204, it is envisioned that an alternative sensor patch according to the disclosure may be provided without such a second adhesive sensor layer 56 and accompanying second sensor release liner 58. Rather, in such an alternative sensor patch, it is envisioned that the distal surface of the sensor patch is the distal surface of the sensor assembly 204, in particular the distal surface of the support layer 214. In such an alternative sensor patch, the distal surface of the support layer 214 may be configured for attachment to the adhesive surface of a base plate. Thus, whereas a sensor patch 50 having a first 52 and a second adhesive sensor layer 56 is illustrated and described, it is envisioned that a similar sensor patch without the second adhesive sensor layer 56 and accompanying second sensor release liner 58 may be provided according to the disclosure.

The sensor patch 50 comprises a stomal opening. The layers of the sensor patch 50, such as the first adhesive sensor layer 52, the support layer 214 and the second adhesive sensor layer 56, as illustrated, may comprise stomal openings 60 for collectively forming the stomal opening of the sensor patch 50. The stomal opening of the sensor patch is configured to be aligned with the stomal opening of the base plate, such as to collectively form the stomal opening of the combined base plate and sensor patch 50.

Figure 3:
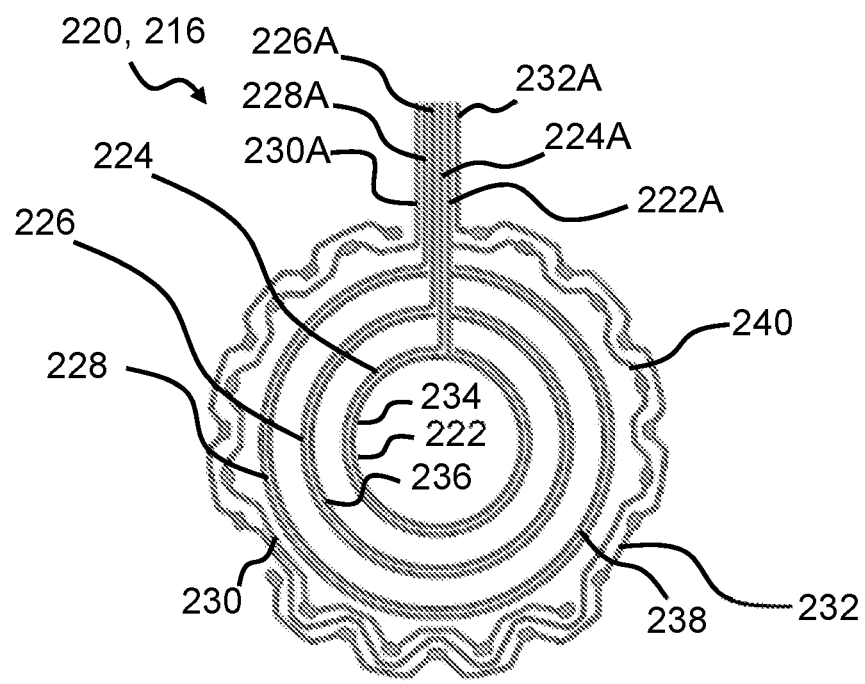

FIG. 3 schematically illustrates an exemplary electrode configuration 220 of electrodes 216 of an exemplary sensor assembly, such as the sensor assembly 204 as described with respect to FIG. 2. The plurality of electrodes 216 comprises a first electrode 222, a second electrode 224, a third electrode 226, a fourth electrode 228, a fifth electrode 230, and a sixth electrode 232.

The first electrode 222 comprises a first connection part 222A and the second electrode 224 comprises a second connection part 224A. The third electrode 226 comprises a third connection part 226A. The fourth electrode 228 comprises a fourth connection part 228A. The fifth electrode 230 comprises a fifth connection part 230A. The sixth electrode 232 comprise a sixth connection part 232A.

The first electrode 222 may be a common ground electrode, such as to form sensors with respect to the remaining electrodes. The first electrode 222 comprises a first electrode part 234 for forming a ground for the second electrode 224. The first electrode 222 comprises a second electrode part 236 for forming a ground for the third electrode 226. The first electrode 222 comprises a third electrode part 238 for forming a ground for the fourth electrode 228. The first electrode 222 comprises a fourth electrode part 240 for forming a ground for the fifth electrode 230 and the sixth electrode 232.

Figure 4:
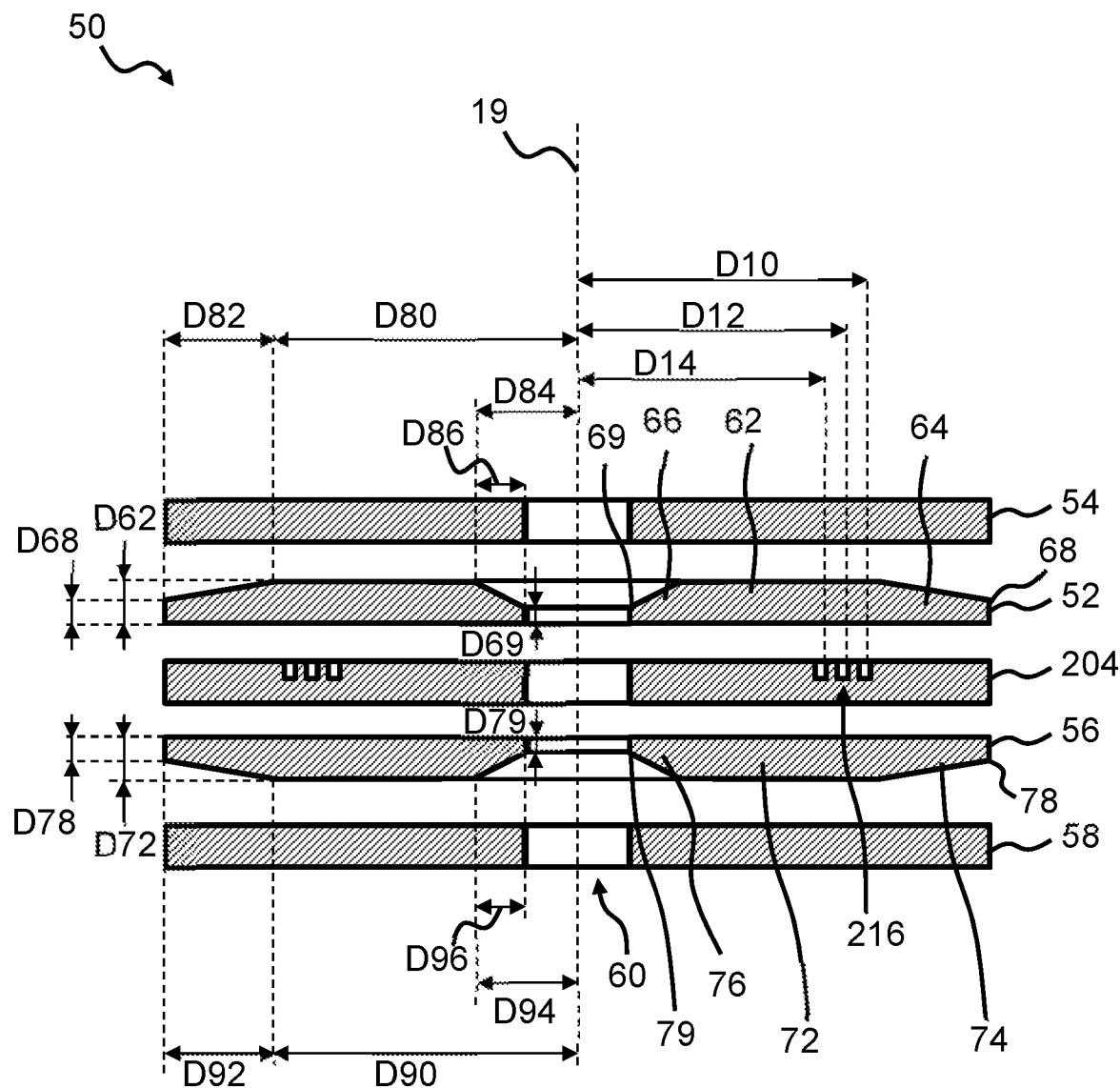

FIG. 4 schematically illustrates a cross section of a sensor patch 50, such as the sensor patch 50 as described with respect to FIG. 2. For illustrative purposes, the layers of the sensor patch 50 are shown separated. The sensor patch 50 comprises a stomal opening 60 with a centre point 19. In some exemplary sensor patches, the stomal opening 60 may be made by the user, i.e. the sensor patch may be manufactured and/or sold without the stomal opening 60, but with a region adapted to form the stomal opening 60 with the centre point 19.

As also described with respect to FIG. 2, the sensor patch 50 comprises sensor assembly 204, and a first adhesive sensor layer 52, a second adhesive sensor layer 56, a first sensor release liner 54, and a second sensor release liner 58. In other exemplary sensor patch, one or more of the first adhesive sensor layer 52, the second adhesive sensor layer 56, the first sensor release liner 54, and the second sensor release liner 58 may be omitted. In particular, whereas the illustrated exemplary sensor patch 50 comprises a second adhesive sensor layer 56 arranged on the distal side of the sensor assembly 204, it is envisioned that an alternative sensor patch according to the disclosure may be provided without such a second adhesive sensor layer 56 and accompanying second sensor release liner 58. Rather, in such an alternative sensor patch, the distal surface of the sensor patch may be the distal surface of the sensor assembly 204.

The first adhesive sensor layer 52 comprises a first centre portion 62. The first adhesive sensor layer 52 comprises a first outer rim portion 64. The first adhesive sensor layer 52 comprises a first inner rim portion 66. The first centre portion 62 surrounds the first inner rim portion 66. The first outer rim portion 64 surrounds the first centre portion 62. The first outer rim portion 64 and the first inner rim portion 66 is the feature also referred to as the chamfered edge of the sensor patch 50. In other words, the chamfered edge of the sensor patch 50 is embodied in the sensor patch through the decreasing/increasing thicknesses of the first outer rim portion 64 and the first inner rim portion 66.

A radial distance D82 of the first outer rim portion 64 is from the first outer rim portion 64 adjacent the first centre portion 62 to the first outer periphery 68 of the first adhesive sensor layer 52. A radial distance D86 of the first inner rim portion 66 is from the first inner periphery 69 of the first adhesive sensor layer 52 to the first centre portion 62, such as to the first centre portion 62 adjacent the first inner rim portion 66. Also shown is a radial distance D84 from the centre point 19 to the first centre portion 62 adjacent the first inner rim portion 66. Also shown is a radial distance D80 from the centre point 19 to the first outer rim portion 64 adjacent the first centre portion 62.

The first centre portion 62 has a first centre thickness D62. The first outer rim portion 64 has a first outer rim thickness decreasing along a radial direction from adjacent the first centre portion 62 to a first outer periphery 68 of the first adhesive sensor layer 52. The first outer rim thickness adjacent the first centre portion 62 is the first centre thickness D62. The first outer rim thickness at the first outer periphery 68 of the first adhesive sensor layer 52 is a first minimum outer rim thickness D68.

The first inner rim portion 66 has a first inner rim thickness increasing along a radial direction from a first inner periphery 69 of the first adhesive sensor layer 52 to the first centre portion 62. The first inner rim thickness adjacent the first centre portion 62 is the first centre thickness D62 and the first inner rim thickness at the first inner periphery 69 of the first adhesive sensor layer 52 is a first minimum inner rim thickness D69.

The second adhesive sensor layer 56 comprises a second centre portion 72. The second adhesive sensor layer 56 comprises a second outer rim portion 74. The second adhesive sensor layer 56 comprises a second inner rim portion 76. The second centre portion 72 surrounds the second inner rim portion 76. The second outer rim portion 74 surrounds the second centre portion 72.

A radial distance D92 of the second outer rim portion 74 is from the second outer rim portion 74 adjacent the second centre portion 72 to the second outer periphery 78 of the second adhesive sensor layer 56. A radial distance D96 of the second inner rim portion 76 from the second inner periphery 79 of the second adhesive sensor layer 56 to the second centre portion 72, such as to the second centre portion 72 adjacent the second inner rim portion 76. Also shown is a radial distance D94 from the centre point 19 to the second centre portion 72 adjacent the second inner rim portion 76. Also shown is a radial distance D90 from the centre point 19 to the second outer rim portion 74 adjacent the second centre portion 72.

The second centre portion 72 has a second centre thickness D72. The second outer rim portion 74 has a second outer rim thickness decreasing along a radial direction from adjacent the second centre portion 72 to a second outer periphery 78 of the second adhesive sensor layer 56. The second outer rim thickness adjacent the second centre portion 72 is the second centre thickness D72. The second outer rim thickness at the second outer periphery 78 of the second adhesive sensor layer 56 is a second minimum outer rim thickness D78.

The second inner rim portion 76 has a second inner rim thickness increasing along a radial direction from a second inner periphery 79 of the second adhesive sensor layer 56 to the second centre portion 72. The second inner rim thickness adjacent the second centre portion 72 is the second centre thickness D72 and the second inner rim thickness at the second inner periphery 79 of the second adhesive sensor layer 56 is a second minimum inner rim thickness D79.

In the illustrated example, the first outer rim thickness, the first inner rim thickness, the second outer rim thickness and the second inner rim thickness is shown to decrease/increase substantially linearly. Alternatively, one or more of the first outer rim thickness, the first inner rim thickness, the second outer rim thickness and the second inner rim thickness may decrease/increase convexly or concavely along the radial direction.

A radial distance D10 from the centre point to a first loop formed by a first electrode of the plurality of electrodes 216 is less than the radial distance D80 from the centre point 19 to the first outer rim portion 64, such as to the first outer rim portion 64 adjacent to the first centre portion 62. The radial distance D10 from the centre point to the first loop is less than the radial distance D90 from the centre point 19 to the second outer rim portion 74, such as to the second outer rim portion 74 adjacent to the second centre portion 72.

A radial distance D12 from the centre point to a second loop formed by a second electrode of the plurality of electrodes 216 is less than the radial distance D80 from the centre point 19 to the first outer rim portion 64, such as to the first outer rim portion 64 adjacent to the first centre portion 62. The radial distance D12 from the centre point to the second loop is less than the radial distance D90 from the centre point 19 to the second outer rim portion 74, such as to the second outer rim portion 74 adjacent to the second centre portion 72. The radial distance D12 from the centre point to the second loop is less than the radial distance D10 from the centre point to the first loop.

A radial distance D14 from the centre point to a third loop formed by a third electrode of the plurality of electrodes 216 is less than the radial distance D80 from the centre point 19 to the first outer rim portion 64, such as to the first outer rim portion 64 adjacent to the first centre portion 62. The radial distance D14 from the centre point to the third loop is less than the radial distance D90 from the centre point 19 to the second outer rim portion 74, such as to the second outer rim portion 74 adjacent to the second centre portion 72. The radial distance D14 from the centre point to the third loop is less than the radial distance D12 from the centre point to the second loop.

Figure 5:
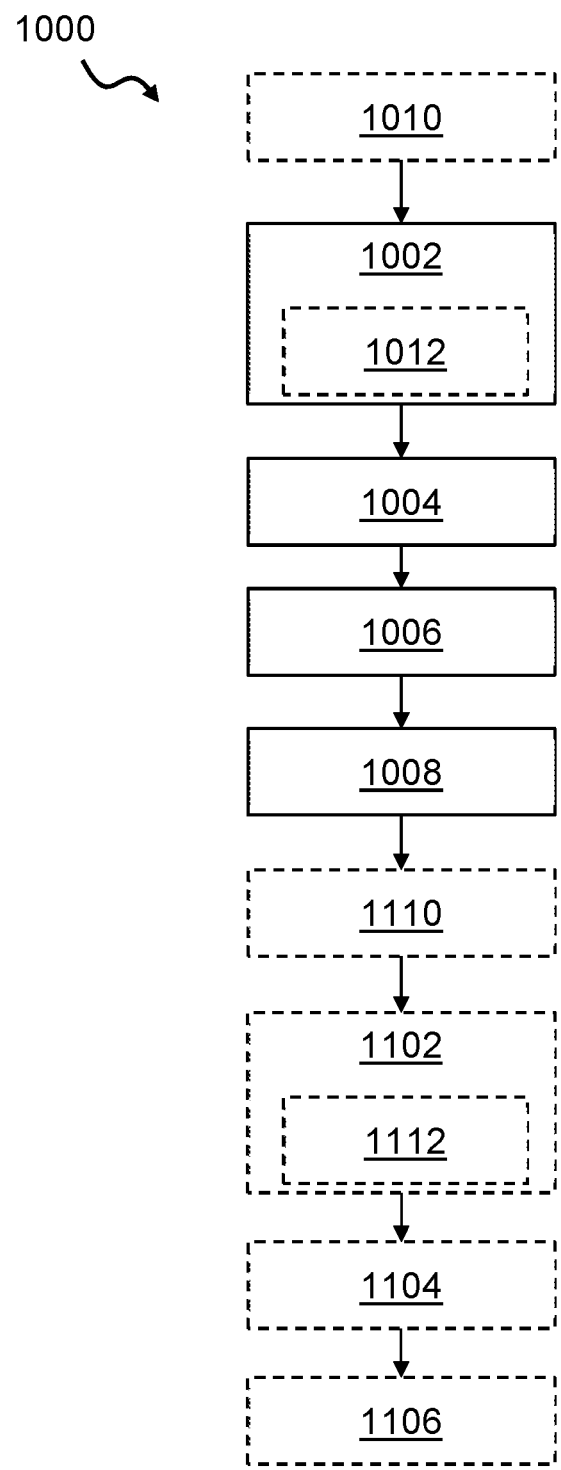
FIG. 5 is a schematic block diagram of an exemplary method.

FIG. 5 is a schematic block diagram of an exemplary method 1000 for manufacturing a sensor patch, such as a sensor patch as described with respect to one or more of the previous figures.

The method 1000 comprises providing 1002 a first adhesive sensor material and laying out 1004 a layer of the first adhesive sensor material for forming a first adhesive sensor layer of the sensor patch. The first adhesive sensor material is laid out 1004 to form a first centre portion and a first outer rim portion surrounding the first centre portion, wherein the first centre portion has a first centre thickness and the first outer rim portion has a first outer rim thickness gradually decreasing along a radial direction from adjacent the first centre portion to the first outer periphery of the first adhesive sensor layer. Further, the first adhesive sensor material is laid out 1004 such that the first outer rim thickness adjacent the first centre portion is the first centre thickness and the first outer rim thickness at the first outer periphery of the first adhesive sensor layer is a first minimum outer rim thickness. Laying out 1004 of the first adhesive sensor material may further comprise forming a first inner rim portion being surrounded by the first centre portion, and wherein the first inner rim portion has a first outer rim thickness gradually increasing along a radial direction from a first inner periphery of the first adhesive sensor layer to the first centre portion adjacent the first inner rim portion.

Laying out 1004 the layer of the first adhesive sensor material for forming the first adhesive sensor layer may comprise extrusion of the first adhesive sensor layer, moulding, such as injection moulding of the first adhesive sensor layer and/or scraping of the first adhesive sensor layer onto a dinted surface. Laying out 1004 the layer of the first adhesive sensor material may comprise a post-process of forming or improving the rim portions.

The method 1000 comprises providing 1006 a sensor assembly comprising a plurality of electrodes, such as the sensor assembly as described with respect to the previous figures. The electrodes including at least a first electrode and a second electrode for forming a first sensor.

The method 1000 comprises arranging 1008 the sensor assembly on a distal side of the first adhesive sensor layer, wherein a proximal side of the first adhesive sensor layer is adapted for attachment of the sensor patch to the skin surface of the user.

The method 1000 optionally comprises providing 1010 a first sensor release liner. Laying out 1004 the layer of the first adhesive sensor material may comprise laying out 1004 the layer of the first adhesive sensor material on a distal side of the first sensor release liner.

Providing 1002 the first adhesive sensor material may optionally comprise sorting 1012 hydrocolloids of the first adhesive sensor material according to grain size. For example, sorting 1012 the hydrocolloids may be done to achieve a smaller average and/or maximum gran size, such as to provide for a thinner rim portion of the first adhesive layer. Alternatively or additionally, laying out 1004 the layer of the first adhesive sensor material may comprise laying out the layer of the first adhesive sensor material for forming the first centre portion with hydrocolloids having a first centre average grain size and/or a first centre maximum grain size, and laying out the layer of the first adhesive sensor material for forming the first outer rim portion and/or the first inner rim portion with hydrocolloids having a first outer rim average grain size and/or a first outer rim average grain size and/or a first inner rim average grain size and/or a first inner rim average grain size, respectively, wherein the first outer rim average/maximum grain size and/or the first inner rim average/maximum grain size is less than the first centre average/maximum grain size. Thereby, the first rim portions may achieve a thinner thickness, e.g. at the peripheries than the first centre portion.

In embodiments, the method 1000 may comprise providing 1102 a second adhesive sensor material and laying out 1104 a layer of the second adhesive sensor material for forming a second adhesive sensor layer of the sensor patch. Whereas the illustrated/disclosed method includes providing 1102 a second adhesive sensor material for forming a second adhesive sensor layer, it is envisioned that an alternative method omits the steps related to such a second adhesive sensor layer, such that the resulting sensor patch has a distal surface being the distal surface of the sensor assembly, and such that the resulting sensor patch has a first adhesive sensor layer only. The second adhesive sensor material is laid out 1104 to form a second centre portion and a second outer rim portion surrounding the second centre portion, wherein the second centre portion has a second centre thickness and the second outer rim portion has a second outer rim thickness gradually decreasing along a radial direction from adjacent the second centre portion to the second outer periphery of the second adhesive sensor layer. Further, the second adhesive sensor material is laid out 1104 such that the second outer rim thickness adjacent the second centre portion is the second centre thickness and the second outer rim thickness at the second outer periphery of the second adhesive sensor layer is a second minimum outer rim thickness. Laying out 1104 of the second adhesive sensor material may further comprise forming a second inner rim portion being surrounded by the second centre portion, and wherein the second inner rim portion has a second outer rim thickness gradually increasing along a radial direction from a second inner periphery of the second adhesive sensor layer to the second centre portion adjacent the second inner rim portion.

Laying out 1104 the layer of the second adhesive sensor material for forming the second adhesive sensor layer may comprise extrusion of the second adhesive sensor layer, moulding, such as injection moulding of the second adhesive sensor layer and/or scraping of the second adhesive sensor layer onto a dinted surface. Laying out 1104 the layer of the second adhesive sensor material may comprise a post-process of forming or improving the rim portions.

The method 1000 optionally comprises providing 1110 a second sensor release liner. Laying out 1104 the layer of the second adhesive sensor material may comprise laying out 1104 the layer of the second adhesive sensor material on a proximal side of the second sensor release liner.

Providing 1102 the second adhesive sensor material may optionally comprise sorting 1112 hydrocolloids of the second adhesive sensor material according to grain size. For example, sorting 1112 the hydrocolloids may be done to achieve a smaller average and/or maximum gran size, such as to provide for a thinner rim portion of the second adhesive layer. Alternatively or additionally, laying out 1104 the layer of the second adhesive sensor material may comprise laying out the layer of the second adhesive sensor material for forming the second centre portion with hydrocolloids having a second centre average/maximum grain size, and laying out the layer of the second adhesive sensor material for forming the second outer rim portion and/or the second inner rim portion with hydrocolloids having a second outer rim average/maximum grain size and/or a second inner rim average/maximum grain size, respectively, wherein the second outer rim average/maximum grain size and/or the second inner rim average/maximum grain size is less than the second centre average/maximum grain size. Thereby, the second rim portions may achieve a thinner thickness, e.g. at the peripheries than the second centre portion.

Providing a sensor patch, wherein the adhesive has a decreasing outer rim and/or an increasing inner rim, facilitates a smoother transition at the interface between the sensor patch and the adhesive surface of the base plate whereto the sensor patch is applied. Thereby, the risk of creating potential creases between the skin of the user and the adhesive surface of the sensor patch and base plate is reduced. Creases between the adhesive surface and the skin of the user could weaken the adhesion and could lead to an increased risk of leakage. Thus, the risk of leakage caused by the sensor patch may be reduced by providing a decreasing outer rim and/or an increasing inner rim.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of body side members for ostomy appliances as discussed herein. Therefore, it is intended that this invention be limited only by the claims and the equivalents thereof.

The invention claimed is:

1. A sensor patch for attachment to a base plate of an ostomy appliance, the sensor patch comprising:
   a sensor assembly layer comprising a plurality of electrodes including a first electrode and a second electrode for forming a first sensor;
   a first adhesive sensor layer forming a distal side of the sensor patch and being adapted for attachment of the distal side of the sensor patch to the proximal surface of the base plate, wherein the first adhesive sensor layer comprises a first centre portion having a first centre thickness and a first outer rim portion surrounding the first centre portion, wherein the first outer rim portion has a first outer rim thickness decreasing along a radial direction from adjacent the first centre portion to a first outer periphery of the first adhesive sensor layer, and wherein the first outer rim thickness adjacent the first centre portion is the first centre thickness and the first outer rim thickness at the first outer periphery of the first adhesive sensor layer is a first minimum outer rim thickness, wherein the sensor patch comprises a stomal opening with a centre point, the stomal opening being configured to allow passage of output through the stomal opening and into an ostomy pouch attached to the base plate.

2. The sensor patch according to claim 1, wherein the first centre thickness is between 0.5 mm and 1.5 mm and the first minimum outer rim thickness is less than 0.5 mm.

3. The sensor patch according to claim 1, wherein a radial distance from the centre point to the first outer rim portion adjacent the centre portion is between 15-35 mm.

4. The sensor patch according to claim 1, wherein a radial distance from the first outer rim portion adjacent the centre portion to the first outer periphery of the first adhesive sensor layer is between 0.5-20 mm.

5. The sensor patch according to claim 1, wherein the first adhesive sensor layer has a first inner rim portion being surrounded by the first centre portion, wherein the first inner rim portion has a first inner rim thickness increasing along a radial direction from a first inner periphery of the first adhesive sensor layer to the first centre portion, and wherein the first inner rim thickness adjacent the first centre portion is the first centre thickness and the first inner rim thickness at the first inner periphery of the first adhesive sensor layer is a first minimum inner rim thickness.

6. The sensor patch according to claim 5, wherein the first minimum inner rim thickness is less than 0.5 mm.

7. The sensor patch according to claim 1, wherein a radial distance from the centre point to the first centre portion adjacent the first inner rim portion is between 10-30 mm.

8. The sensor patch according to claim 1, wherein a radial distance of the first inner rim portion from the first inner periphery of the first adhesive sensor layer to the first centre portion is between 0.5-20 mm.

9. The sensor patch according to claim 1, wherein the first adhesive sensor layer comprises hydrocolloids.

10. The sensor patch according to claim 9, wherein the hydrocolloids are arranged such that the hydrocolloids being arranged along the first outer periphery of the first adhesive sensor layer have a first outer rim average grain size, and wherein the hydrocolloids arranged in the first centre portion have a first centre average gran size, and wherein the first outer rim average grain size is less than the first centre average grain size.

11. The sensor patch according to claim 10, wherein the first outer rim average grain size is less than half of the first centre average grain size.

12. The sensor patch according to claim 9, wherein the hydrocolloids have an average grain size of less than 0.2 mm.

13. The sensor patch according to claim 1, comprising a first sensor release liner arranged to protect the first adhesive sensor layer and configured to be peeled off by the user prior to application of the base plate with the attached sensor patch to the skin.

14. The sensor patch according to claim 1, wherein the first electrode forms a first loop surrounding the centre point, and wherein a radial distance from the centre point to the first loop is less than the radial distance from the centre point to the first outer rim portion.

15. The sensor patch according to claim 14, wherein the second electrode forms a second loop surrounding the centre point, and wherein a radial distance from the centre point to the second loop is less than the radial distance from the centre point to the first loop.

16. The sensor patch according to claim 1, wherein the first outer rim thickness is decreasing convexly along the radial direction from adjacent the first centre portion to the first outer periphery of the first adhesive sensor layer.

17. The sensor patch according to claim 1, wherein the first outer rim thickness is decreasing concavely along the radial direction from adjacent the first centre portion to the first outer periphery of the first adhesive sensor layer.

18. The sensor patch according to claim 1, wherein the first outer rim thickness is decreasing substantially linearly along the radial direction from adjacent the first centre portion to the first outer periphery of the first adhesive sensor layer.

19. A method for manufacturing a sensor patch, the method comprising:
   providing a first adhesive sensor material;
   laying out a layer of the first adhesive sensor material for forming a first adhesive sensor layer of the sensor patch, wherein the first adhesive sensor material is laid out to form a first centre portion and a first outer rim portion surrounding the first centre portion, wherein the first centre portion has a first centre thickness and the first outer rim portion has a first outer rim thickness gradually decreasing along a radial direction from adjacent the first centre portion to the first outer periphery of the first adhesive sensor layer, and wherein the first outer rim thickness adjacent the first centre portion is the first centre thickness and the first outer rim thickness at the first outer periphery of the first adhesive sensor layer is a first minimum outer rim thickness;
   providing a sensor assembly comprising a plurality of electrodes including a first electrode and a second electrode for forming a first sensor; and
   arranging the sensor assembly on a distal side of the first adhesive sensor layer, wherein a proximal side of the first adhesive sensor layer is adapted for attachment of the sensor patch to the skin surface of a user and a distal side of the sensor patch is adapted for attachment to an adhesive surface of a base plate, the adhesive surface of the base plate being adapted for attachment to a skin surface of the user.

20. The method according to claim 19, comprising providing a first sensor release liner, and wherein laying out the layer of the first adhesive sensor material comprises laying out the layer of the first adhesive sensor material on a distal side of the first sensor release liner.

21. The method according to claim 19, wherein providing the first adhesive sensor material comprises sorting hydrocolloids of the first adhesive sensor material according to grain size.

22. The method according to claim 21, wherein laying out the layer of the first adhesive sensor material comprises laying out the layer of the first adhesive sensor material for forming the first centre portion with hydrocolloids having a first centre average grain size, and laying out the layer of the first adhesive sensor material for forming the first outer rim portion with hydrocolloids having a first outer rim average grain size, wherein the first outer rim average grain size is less than the first centre average grain size.

23. The method according to claim 21, wherein sorting the hydrocolloids comprises sorting the hydrocolloids to achieve an average grain size of the hydrocolloids of less than 0.2 mm.

24. The method according to claim 19, wherein laying out the layer of the first adhesive sensor material for forming the first adhesive sensor layer comprises extruding the first adhesive sensor layer.

25. The method according to claim 19, wherein laying out the layer of the first adhesive sensor material for forming the first adhesive sensor layer comprises moulding, such as injection moulding, of the first adhesive sensor layer, wherein the mould has a non-planar surface shaped to provide the first outer rim thickness gradually decreasing along the radial direction from adjacent the first centre portion to the first outer periphery of the first adhesive sensor layer.

26. The method according to claim 19, wherein laying out the layer of the first adhesive sensor material for forming the first adhesive sensor layer comprises scraping the first adhesive sensor material onto a non-planar surface shaped to provide the first outer rim thickness gradually decreasing along the radial direction from adjacent the first centre portion to the first outer periphery of the first adhesive sensor layer.

27. The sensor patch according to claim 1, wherein the sensor patch is sized to expose an outer portion of the adhesive surface of the base plate, thereby enabling adhesion by the outer portion of the adhesive surface of the base plate to the skin surface of the user, in addition to adhesion by the first adhesive sensor layer of the sensor patch.

* * * * *